US008754009B2

(12) United States Patent
Stenzel et al.

(10) Patent No.: US 8,754,009 B2
(45) Date of Patent: Jun. 17, 2014

(54) ACTIVE COMPOUND COMBINATIONS

(75) Inventors: Klaus Stenzel, Düsseldorf (DE); Markus Dollinger, Lyons (FR); Peter Dahmen, Neuss (DE); Ulrike Wachendorff-Neumann, Neuwied (DE); Isolde Häuser-Hahn, Leverkusen (DE); Marie-Claire Grosjean, Curis au Mont d'Or (FR); Bernard Marc Leroux, Morance (FR); Haruko Sawada, Yuki (JP); Hiroyuki Hadano, Tochigi (JP); Jean-Marie Gouot, Saint-Cyr au Mont d'Or (FR); Christian Scherb, Stad Campinas (BR)

(73) Assignee: Bayer CropScience AG, Monheim (DE)

( * ) Notice: Subject to any disclaimer, the term of this patent is extended or adjusted under 35 U.S.C. 154(b) by 945 days.

(21) Appl. No.: 11/921,667

(22) PCT Filed: May 27, 2006

(86) PCT No.: PCT/EP2006/005094
§ 371 (c)(1),
(2), (4) Date: Jun. 15, 2009

(87) PCT Pub. No.: WO2006/131230
PCT Pub. Date: Dec. 14, 2006

(65) Prior Publication Data
US 2011/0152097 A1    Jun. 23, 2011

(30) Foreign Application Priority Data

Jun. 9, 2005  (DE) .......................... 10 2005 026 482
Jun. 9, 2005  (DE) .......................... 10 2005 026 483

(51) Int. Cl.
*A01N 57/00*    (2006.01)
*A61K 31/675*    (2006.01)

(52) U.S. Cl.
USPC .............................. 504/128; 514/92; 514/93

(58) Field of Classification Search
None
See application file for complete search history.

(56) References Cited

U.S. PATENT DOCUMENTS

| 4,245,432 | A | | 1/1981 | Dannelly |
| 4,272,417 | A | | 6/1981 | Barke et al. |
| 4,742,060 | A | | 5/1988 | Shiokawa et al. |
| 4,808,430 | A | | 2/1989 | Kouno |
| 4,849,432 | A | | 7/1989 | Shiokawa et al. |
| 5,110,805 | A | | 5/1992 | Berner et al. |
| 5,852,012 | A | | 12/1998 | Maienfisch et al. |
| 5,876,739 | A | | 3/1999 | Turnblad et al. |
| 5,969,213 | A | * | 10/1999 | Adams et al. .................. 800/300 |
| 6,407,316 | B1 | | 6/2002 | Holmes et al. |
| 2002/0094934 | A1 | | 7/2002 | Hacker et al. |
| 2002/0198222 | A1 | | 12/2002 | Bruns et al. |
| 2003/0060371 | A1 | * | 3/2003 | Asrar et al. .................. 504/272 |
| 2003/0176428 | A1 | | 9/2003 | Schneidersmann et al. |
| 2004/0248955 | A1 | | 12/2004 | Wachendorff-Neumann et al. |
| 2005/0032903 | A1 | * | 2/2005 | Suarez-Cervieri et al. ... 514/620 |
| 2005/0223425 | A1 | * | 10/2005 | Clinton et al. ................ 800/279 |
| 2008/0132413 | A1 | | 6/2008 | Deall et al. |
| 2009/0018015 | A1 | | 1/2009 | Wachendorff-Neumann et al. |
| 2011/0105577 | A1 | | 5/2011 | Meissner et al. |

FOREIGN PATENT DOCUMENTS

| DE | 100 59 609 A1 | 6/2002 |
| EP | 0 150 959 A2 | 8/1985 |
| EP | 0 192 060 A1 | 8/1986 |
| EP | 0 192 606 A2 | 8/1986 |
| EP | 0 235 725 A2 | 9/1987 |
| EP | 0 302 389 A2 | 2/1989 |
| EP | 0 376 279 A2 | 7/1990 |
| EP | 0 431 545 A2 | 6/1991 |
| EP | 0 431 545 A3 | 6/1991 |
| EP | 0 580 553 A2 | 1/1994 |
| EP | 0 649 845 A1 | 4/1995 |
| EP | 0 945 065 A1 | 9/1999 |
| GB | 2 313 595 A | 12/1997 |
| HU | 203 453 B | 8/1991 |
| RU | 2 251 270 C2 | 5/2005 |
| WO | WO 91/04965 A1 | 4/1991 |
| WO | WO 99/09830 A1 | 3/1999 |
| WO | WO 99/35913 A1 | 7/1999 |
| WO | WO 99/45781 A1 | 9/1999 |
| WO | WO 00/78142 A2 | 12/2000 |
| WO | WO 02/28184 A1 | 4/2002 |
| WO | WO 02/28186 A2 | 4/2002 |

(Continued)

OTHER PUBLICATIONS

Hérouet et al. "Safety evaluation of the phosphinothricin acetyltransferase proteins encoded by the pat and bar sequences that confer tolerance to glufosinate-ammonium herbicide in transgenic plants", Regulatory Toxicology and Pharmacology, 41, Mar. 2005, p. 134-149.*

(Continued)

*Primary Examiner* — Tracy Vivlemore
*Assistant Examiner* — Monica Shin
(74) *Attorney, Agent, or Firm* — Sterne, Kessler, Goldstein & Fox P.L.L.C.

(57) ABSTRACT

The present invention relates to novel active compound combinations comprising, firstly, a known herbicide selected from the group consisting of glyphosate, glufosinate and glufosinate-ammonium and, secondly, at least one known fungicidally active compound, which combination is highly suitable for controlling unwanted phytopathogenic fungi, in particular soya bean rust. Particular preference is given to using these mixtures on transgenic plants resistant to the herbicides mentioned.

27 Claims, No Drawings

(56) References Cited

FOREIGN PATENT DOCUMENTS

| WO | WO 02/30205 A2 | 4/2002 |
|---|---|---|
| WO | WO 02/080675 A1 | 10/2002 |
| WO | WO 02/094020 A1 | 11/2002 |
| WO | WO 03/017760 A2 | 3/2003 |
| WO | WO 03/017762 A2 | 3/2003 |
| WO | WO 2004/043150 A1 | 5/2004 |
| WO | WO 2005/041653 A2 | 5/2005 |
| WO | WO 2005/041669 A1 | 5/2005 |
| WO | WO 2005/044002 A2 | 5/2005 |
| WO | WO 2005/102057 A2 | 11/2005 |
| WO | WO 2005/102057 A3 | 11/2005 |
| WO | WO 2006/128095 A2 | 11/2006 |

OTHER PUBLICATIONS

Alanwood.net, "Fluoxastrobin", <http://www.alanwood.net/pesticides/fluoxastrobin.html>, Feb. 21, 2004; p. 1.*
Database CA, Chemical Abstracts Service, Accession No. 125:107758, El-Sayed, et al., Journal of Agricultural Science (1996), 126, pp. 463-469.
Database CABA on STN International, Accession No. 1998:41822, Szilvasi, Journees Internationales sur la Lutte Contre les Mauvaises Herbes (1996), pp. 983-989.
Database CROPU on STN International, Accession No. 2002:84406, Fitterer, S.A., et al., Res. Prog. Rep. West. Soc. Weed. Sci. (2001), pp. 41-42.
Database CROPU on STN International, Accession No. 2000:82254, Thorsness, K.B., et al., Proc. North. Cent. Weed. Sci. Soc. (1998), pp. 136-137.
English language Abstract of DE 100 59 609 A1, European Patent Office, espacenet database—Worldwide, (2000).
English language Abstract of EP 0 431 545 A2, European Patent Office, espacenet database—Worldwide, (1991).
International Preliminary Report on Patentability for International Application No. PCT/EP2006/005094, issued Jan. 29, 2008, European Patent Office, Switzerland.
English language Abstract of HU 203 453 B, European Patent Office, espacenet database—Worldwide (1991).
Monsanto Company, "Roundup Custom," Updates Available at www.greenbook.net, C&P Press, pp. 1-15 (2000).
Monsanto Company, "Roundup Ultramax RT," Updates Available at www.greenbook.net, C&P Press, pp. 1-15 (2001).
Syngenta Crop Protection UK Ltd., "Touchdown," Safety Data Sheet, Issue Date Jul. 17, 2002, pp. 1-4.
A data sheet from the Compendium of Pesticide Common Names, "Azoxystrobin," www.alanwood.net/pesticides/azoxystrobin.html, Sep. 17, 2009.
Annex to Office Action for EP Patent Application No. 06 791 516.5, issued Mar. 30, 2009 (German).
Annex to Office Action for EP Patent Application No. 06 791 516.5, issued Mar. 30, 2009, partial English translation.
Response to Office Action for EP Patent Application No. 06 791 516.5, (German), filed Sep. 18, 2009.
Response to Office Action for EP patent No. 06 791 516.5, English translation, filed Sep. 18, 2009.
Szilvasi, Sophie, "Mildiou: Soigner La Protection Au Défanage," Phytoma—La Défense des végétaux—N° 472 (1995).
European Search Report for International Application No. EP 10 16 9113, European Patent Office (Oct. 2010).
European Search Report for International Application No. EP 09 17 0708, European Patent Office (Jan. 2010).
European Search Report for International Application No. EP 10 16 9140, European Patent Office (Oct. 2010).
European Search Report for International Application No. EP 10 16 9131, European Patent Office (Oct. 2010).
Anonymous, "Mixtures of Fungicides and Herbicides" Research Disclosure No. 34874, Kenneth Mason Publications Ltd., 4 pages (1993).
Anonymous, "Mixtures of Fungicides and Insecticides" Research Disclosure No. 33893, Kenneth Mason Publications Ltd., 9 pages (1993).
Ramsdale, B.K., et al., "Glyphosate tank-mixed with insecticides or fungicides," NCWSS Research Report 59:280-283, The Society, Champaign, IL, US (2002).
Database WPI, Accession No. 1989-215139, "Synergistic fungicide and plant growth controlling agent-contains carbamoyl-phosphonate and N-phosphono-methyl-glycine or salts," Alkaloida Vegyeszeti Gyar (1989), abstract.
Dialog File 351, Accession No. 12632097, Derwent WPI English language abstract for DE 100 59 609 (listed on accompanying PTO/SB/08A as document FP16), Feb. 7, 2008.
Database CAPLUS, Chemical Abstracts Service, Accession No. 1997:514138, Mascarenhas, V.J., and Griffin, J.L., 2 pages (1997).
Database CAPLUS, Chemical Abstracts Service, Accession No. 2004:778117, McAllister, C.D., et al., 2 pages (2003).
Database CAPLUS, Chemical Abstracts Service, Accession No. 1999:429857, Pankey, J.H., et al., 2 pages (1999).
International Search Report for International Application PCT/EP2006/005094, European Patent Office, Netherlands, mailed on Nov. 2, 2007.
International Search Report for International Application No. PCT/EP2005/007947, European Patent Office, Netherlands, mailed on Oct. 4, 2005.
Dialog File 351, Accession No. 5567045, Derwent WPI English language abstract for EP 0 431 545 A2 & A3 (listed on accompanying PTO/SB/08A as document FP6), Mar. 10, 2008.
Office Action mailed Jan. 29, 2013, for U.S. Appl. No. 12/745,450, Int'l Filing Date Nov. 15, 2008, U.S. Patent and Trademark Office, Alexandria, VA.
Office Action mailed Sep. 18, 2013, for U.S. Appl. No. 12/745,450, Int'l Filing Date Nov. 15, 2008, U.S. Patent and Trademark Office, Alexandria, VA.

* cited by examiner

ACTIVE COMPOUND COMBINATIONS

This application is a 35 U.S.C. §371 U.S. National Phase filing of International Application No. PCT/EP2006/005094, filed May 27, 2006, which claims the benefit of German Patent Application Nos. 10 2005 026 482.4 and 10 2005 026 483.2, both filed Jun. 9, 2005. Each application is incorporated by reference herein in its entirety.

The present invention relates to novel active compound combinations comprising, firstly, a known herbicide selected from the group consisting of glyphosate, glufosinate and glufosinate-ammonium and, secondly, at least one known fungicidally active compound, which combination is highly suitable for controlling unwanted phytopathogenic fungi, in particular soya bean rust. Particular preference is given to using these mixtures on transgenic plants resistant to the herbicides mentioned.

It is already known that glyphosate, glufosinate and glufosinate-ammonium have herbicidal properties (cf. DE-A 21 52 826, DE-A 27 17 440). Furthermore, it is known that numerous carboxamides, triazole derivatives, aniline derivatives, dicarboximides and other heterocycles can be used for controlling fungi (cf. WO 03/010149, DE-A 103 03 589, EP-A 0 040 345, DE-A 22 01 063, DE-A 23 24 010, Pesticide Manual, 9th. Edition (1991), pages 249 and 827, EP-A 0 382 375 and EP-A 0 515 901). However, at low application rates the activity of these compounds is not always satisfactory. Furthermore, it is already known that 1-(3,5-dimethylisoxazole-4-sulphonyl)-2-chloro-6,6-difluoro-[1,3]-dioxolo-[4,5f]-benzimidazole has fungicidal properties (cf. WO 97/06171). Finally, it is also known that substituted halopyrimidines have fungicidal properties (cf. DE-A 196 46 407, EP-B-712 396).

This invention now provides novel active compound combinations having very good fungicidal properties and comprising Group (1) a herbicide selected from (1-1) glyphosate (known from DE-A 21 52 826) of the formula

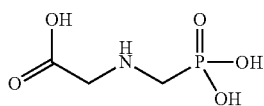

(1-2) glufosinate (known from DE-A 27 17 440) of the formula

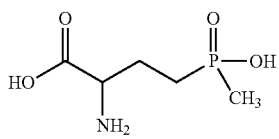

(1-3) glufosinate-ammonium (known from Pesticide Manual, 13 Edition, British Crop Protection Council, 2003, pages 511-512) of the formula

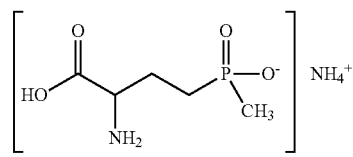

and at least one active compound selected from groups (2) to (23) below:

Group (2) strobilurins selected from (2-1) azoxystrobin (known from EP-A 0 382 375) of the formula

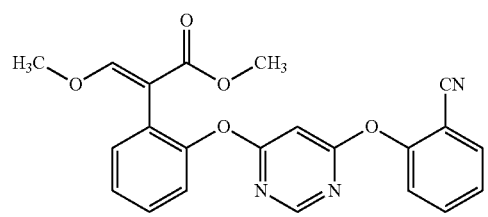 [SMILES: CO/C=C(/C(=O)OC)c1ccccc1Oc1cc(Oc2ccccc2C#N)ncn1]

(2-2) fluoxastrobin (known from DE-A 196 02 095) of the formula

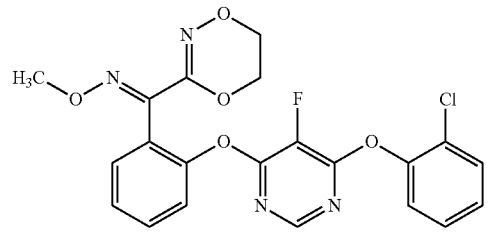 [SMILES: CO/N=C(/C1=NOCCO1)c1ccccc1Oc1ncnc(Oc2ccccc2Cl)c1F]

(2-3) (2E)-2-(2-{[6-(3-chloro-2-methylphenoxy)-5-fluoro-4-pyrimidinyl]oxy}phenyl)-2-(methoxyimino)-N-methylethanamide (known from DE-A 196 46 407) of the formula

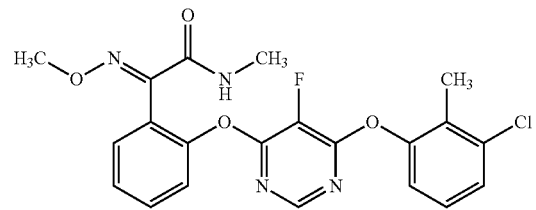 [SMILES: CNC(=O)/C(=N/OC)c1ccccc1Oc1ncnc(Oc2cccc(Cl)c2C)c1F]

(2-4) trifloxystrobin (known from EP-A 0 460 575) of the formula

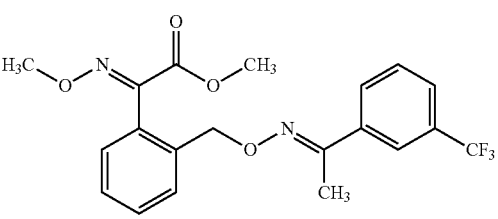 [SMILES: CO/N=C(/C(=O)OC)c1ccccc1CO/N=C(\C)c1cccc(C(F)(F)F)c1]

(2-5) (2E)-2-(methoxyimino)-N-methyl-2-(2-{[({(1E)-1-[3-(trifluoromethyl)phenyl]ethylidene}-amino)oxy]methyl}phenyl)ethanamide (known from EP-A 0 569 384) of the formula

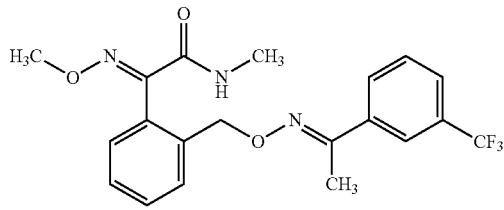 [SMILES: CNC(=O)/C(=N/OC)c1ccccc1CO/N=C(\C)c1cccc(C(F)(F)F)c1]

(2-6) (2E)-2-(methoxyimino)-N-methyl-2-{2-[(E)-({1-[3-(trifluoromethyl)phenyl]ethoxy}imino)-methyl]phenyl}ethanamide (known from EP-A 0 596 254) of the formula

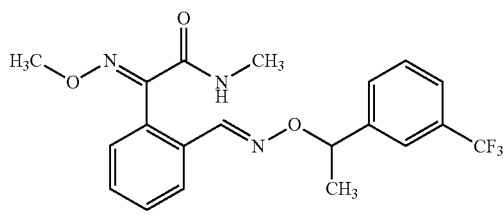 [SMILES: CNC(=O)/C(=N/OC)c1ccccc1/C=N/OC(C)c1cccc(C(F)(F)F)c1]

(2-7) orysastrobin (known from DE-A 195 39 324) of the formula

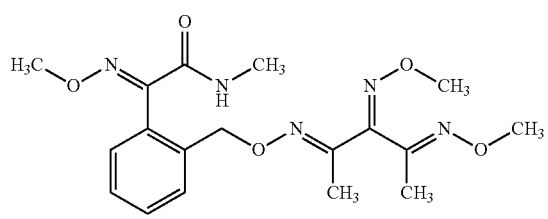

(2-8) 5-methoxy-2-methyl-4-(2-{[({(1E)-1-[3-(trifluoromethyl)phenyl]ethylidene}amino)oxy]-methyl}phenyl)-2,4-dihydro-3H-1,2,4-triazol-3-one (known from WO 98/23155) of the formula

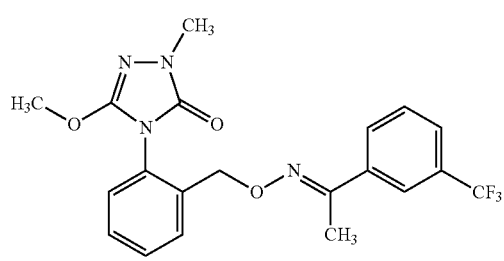 [SMILES: COc1nn(C)c(=O)n1-c1ccccc1CO/N=C(\C)c1cccc(C(F)(F)F)c1]

(2-9) kresoxim-methyl (known from EP-A 0 253 213) of the formula

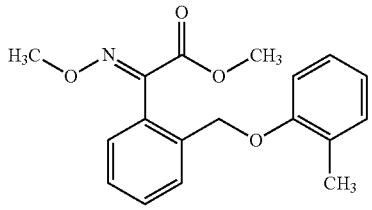 [SMILES: CO/N=C(/C(=O)OC)c1ccccc1COc1ccccc1C]

(2-10) dimoxystrobin (known from EP-A 0 398 692) of the formula

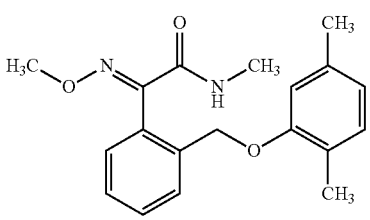 [SMILES: CNC(=O)/C(=N/OC)c1ccccc1COc1cc(C)ccc1C]

(2-11) picoxystrobin (known from EP-A 0 278 595) of the formula

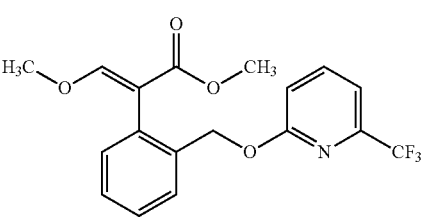 [SMILES: CO/C=C(/C(=O)OC)c1ccccc1COc1cccc(C(F)(F)F)n1]

(2-12) pyraclostrobin (known from DE-A 44 23 612) of the formula

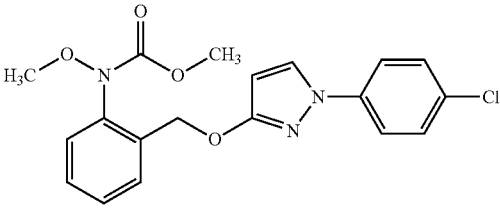 [SMILES: COC(=O)N(OC)c1ccccc1COc1ccn(-c2ccc(Cl)cc2)n1]

(2-13) metominostrobin (known from EP-A 0 398 692) of the formula

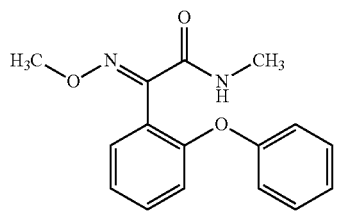 [SMILES: CNC(=O)/C(=N/OC)c1ccccc1Oc1ccccc1]

(2-14) (2E)-2-{2-[({[(1E)-1-(3-{[(E)-1-fluoro-2-phenylvinyl]oxy}phenyl)ethylidene]amino}oxy)-methyl]phenyl}-2-(methoxyimino)-N-methylacetamide (known from WO 01/12585) of the formula

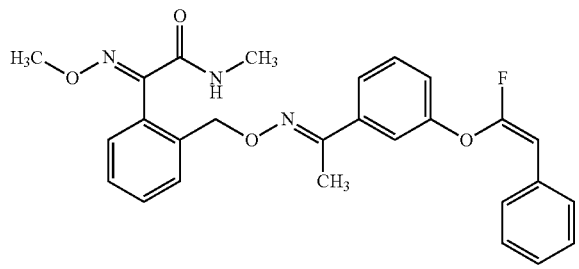 [SMILES: CNC(=O)/C(=N/OC)c1ccccc1CO/N=C(\C)c1cccc(O/C(F)=C\c2ccccc2)c1]

(2-15) enestrobin (known from EP-A 0 936 213) of the formula

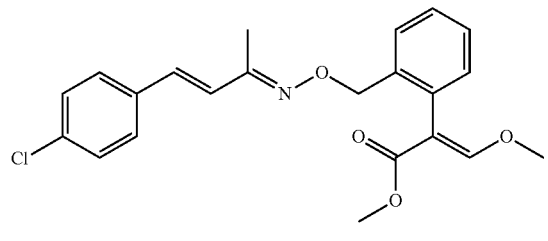 [SMILES: CO/C=C(/C(=O)OC)c1ccccc1CO/N=C(C)/C=C/c1ccc(Cl)cc1]

Group (3) triazoles selected from (3-1) azaconazole (known from DE-A 25 51 560) of the formula

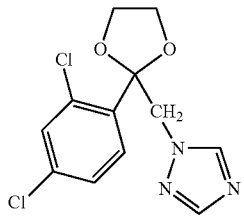 [SMILES: Clc1ccc(C2(Cn3cncn3)OCCO2)c(Cl)c1]

(3-2) etaconazole (known from DE-A 25 51 560) of the formula

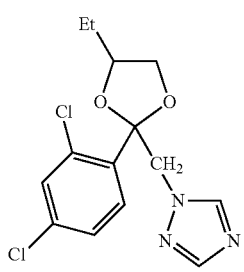 [SMILES: CCC1COC(Cn2cncn2)(c2ccc(Cl)cc2Cl)O1]

(3-3) propiconazole (known from DE-A 25 51 560) of the formula

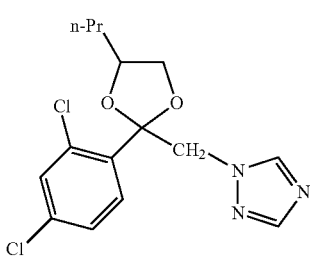

(3-4) difenoconazole (known from EP-A 0 112 284) of the formula

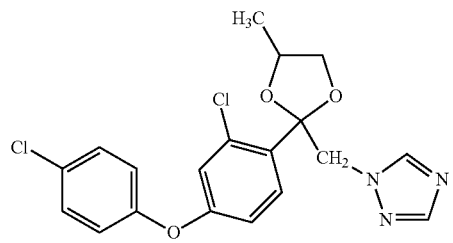 [SMILES: CC1COC(Cn2cncn2)(c2ccc(Oc3ccc(Cl)cc3)cc2Cl)O1]

(3-5) bromuconazole (known from EP-A 0 258 161) of the formula

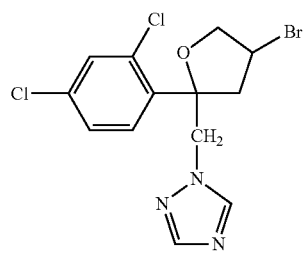 [SMILES: Clc1ccc(C2(Cn3cncn3)CC(Br)CO2)c(Cl)c1]

(3-6) cyproconazole (known from DE-A 34 06 993) of the formula

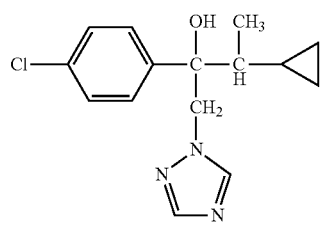 [SMILES: CC(C1CC1)C(O)(Cn1cncn1)c1ccc(Cl)cc1]

(3-7) hexaconazole (known from DE-A 30 42 303) of the formula

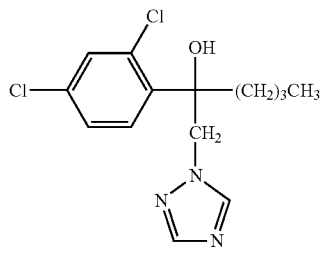

(3-8) penconazole (known from DE-A 27 35 872) of the formula

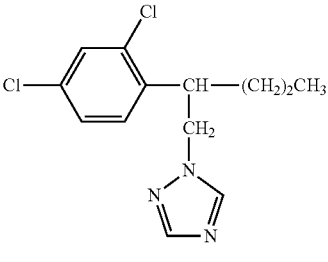

(3-9) myclobutanil (known from EP-A 0 145 294) of the formula

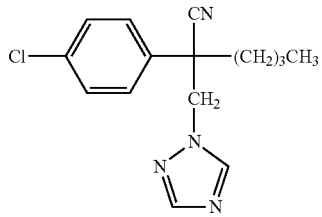

(3-10) tetraconazole (known from EP-A 0 234 242) of the formula

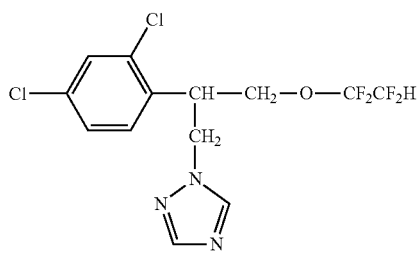

(3-11) flutriafol (known from EP-A 0 015 756) of the formula

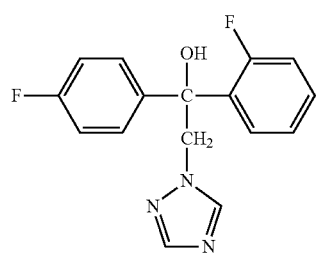 [SMILES: OC(Cn1cncn1)(c1ccc(F)cc1)c1ccccc1F]

(3-12) epoxiconazole (known from EP-A 0 196 038) of the formula

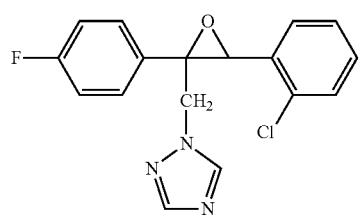 [SMILES: Fc1ccc(C2(Cn3cncn3)OC2c2ccccc2Cl)cc1]

(3-13) flusilazole (known from EP-A 0 068 813) of the formula

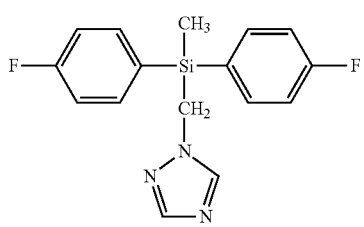 [SMILES: C[Si](Cn1cncn1)(c1ccc(F)cc1)c1ccc(F)cc1]

(3-14) simeconazole (known from EP-A 0 537 957) of the formula

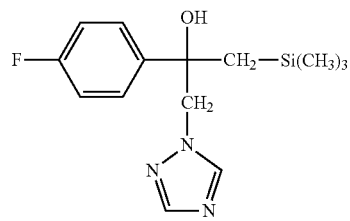

(3-15) prothioconazole (known from WO 96/16048) of the formula

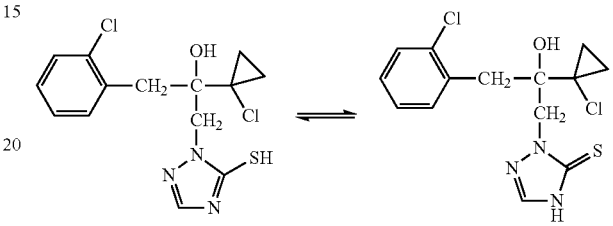

(3-16) fenbuconazole (known from DE-A 37 21 786) of the formula

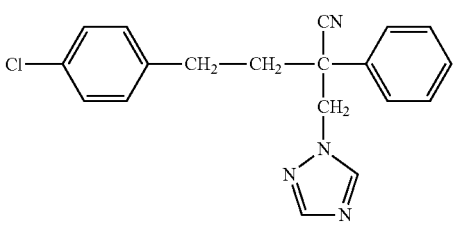 [SMILES: N#CC(CCc1ccc(Cl)cc1)(Cn1cncn1)c1ccccc1]

(3-17) tebuconazole (known from EP-A 0 040 345) of the formula

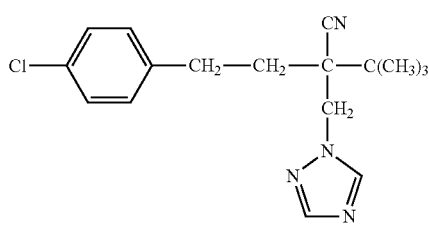 [SMILES: CC(C)(C)C(C#N)(CCc1ccc(Cl)cc1)Cn1cncn1]

(3-18) ipconazole (known from EP-A 0 329 397) of the formula

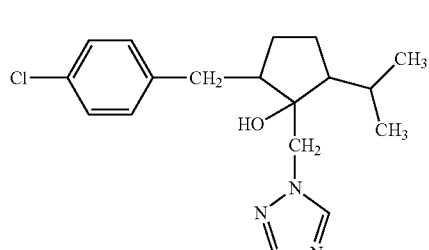

(3-19) metconazole (known from EP-A 0 329 397) of the formula (3-20) triticonazole (known from EP-A 0 378 953) of the formula

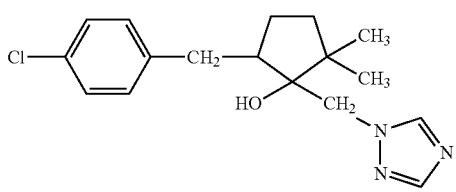 [SMILES: CC1(C)CCC(Cc2ccc(Cl)cc2)C1(O)Cn1cncn1]

(3-21) bitertanol (known from DE-A 23 24 010) of the formula

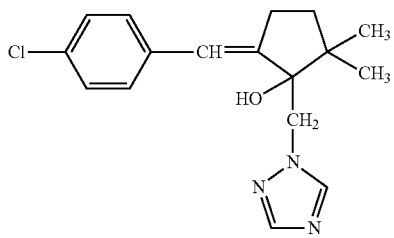 [SMILES: CC1(C)CCC(=Cc2ccc(Cl)cc2)C1(O)Cn1cncn1]

(3-22) triadimenol (known from DE-A 23 24 010) of the formula

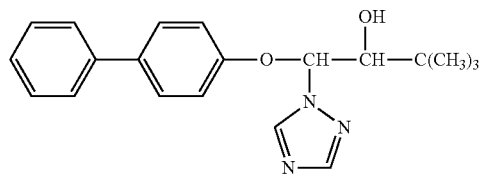 [SMILES: CC(C)(C)C(O)C(Oc1ccc(-c2ccccc2)cc1)n1cncn1]

(3-23) triadimefon (known from DE-A 22 01 063) of the formula

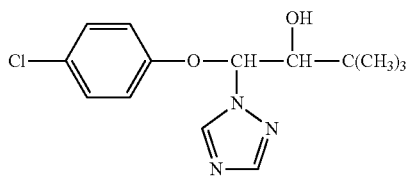 [SMILES: CC(C)(C)C(O)C(Oc1ccc(Cl)cc1)n1cncn1]

(3-24) fluquinconazole (known from EP-A 0 183 458) of the formula (3-25) quinconazole (known from EP-A 0 183 458) of the formula

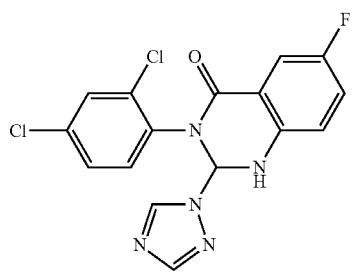 [SMILES: O=C1c2cc(F)ccc2NC(n2cncn2)N1c1ccc(Cl)cc1Cl]

(3-26) amisulbrom (known from JP-A 2001-187786) of the formula

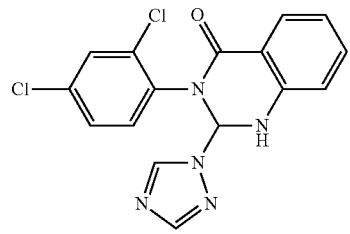 [SMILES: O=C1c2ccccc2NC(n2cncn2)N1c1ccc(Cl)cc1Cl]

Group (4) sulphenamides/sulphonamides selected from (4-1) dichlofluanid (known from DE-A 11 93 498) of the formula

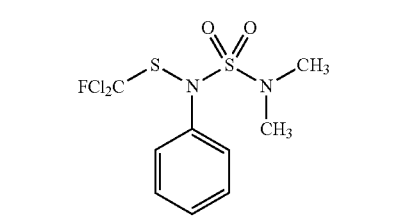

(4-2) tolylfluanid (known from DE-A 11 93 498) of the formula

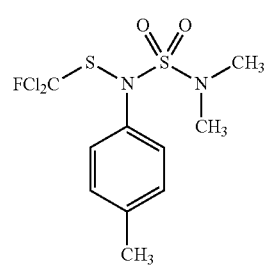

(4-3) N-(4-chloro-2-nitrophenyl)N-ethyl-4-methylbenzene sulphonamide (known from WO 00/659513) of the formula

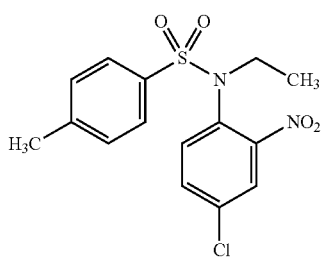 [SMILES: CCN(c1ccc(Cl)cc1[N+](=O)[O-])S(=O)(=O)c1ccc(C)cc1]

Group (5) valinamides selected from
(5-1) iprovalicarb (known from DE-A 40 26 966) of the formula

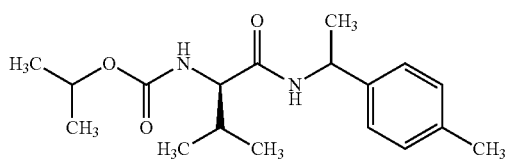 [SMILES: Cc1ccc(C(C)NC(=O)[C@H](NC(=O)OC(C)C)C(C)C)cc1]

(5-2) N$^1$-[2-(4-{[3-(4-chlorophenyl)-2-propynyl]oxy}-3-methoxyphenyl)ethyl]-N$^2$-(methylsulphonyl)-L-valinamide
(5-3) benthiavalicarb (known from WO 96/04252) of the formula

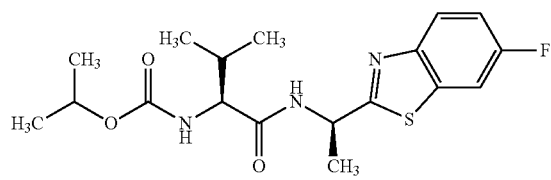 [SMILES: CC(C)OC(=O)N[C@H](C(=O)N[C@H](C)c1nc2ccc(F)cc2s1)C(C)C]

Group (6) carboxamides selected from
(6-1) N-[2-(1,3-dimethylbutyl)phenyl]-1,3-dimethyl-1H-pyrazole-4-carboxamide (known from JP-A 10-251240) of the formula

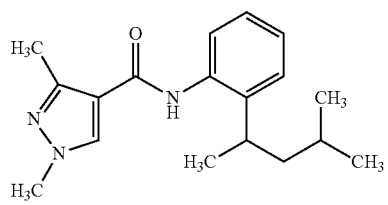 [SMILES: Cc1nn(C)cc1C(=O)Nc1ccccc1C(C)CC(C)C]

(6-2) N-[2-(1,3-dimethylbutyl)phenyl]-5-fluoro-1,3-dimethyl-1H-pyrazole-4-carboxamide (known from WO 03/010149) of the formula

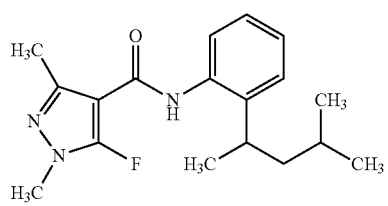

(6-3) N-[2-(1,3-dimethylbutyl)phenyl]-5-chloro-1,3-dimethyl-1H-pyrazole-4-carboxamide (known from JP-A 10-251240) of the formula

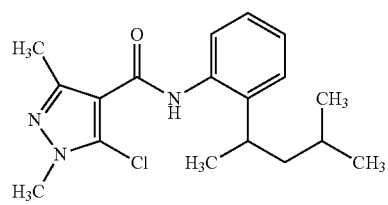 [SMILES: Cc1nn(C)c(Cl)c1C(=O)Nc1ccccc1C(C)CC(C)C]

(6-4) 3-(difluoromethyl)-N-[2-(1,3-dimethylbutyl)phenyl]-1-methyl-1H-pyrazole-4-carboxamide of the formula

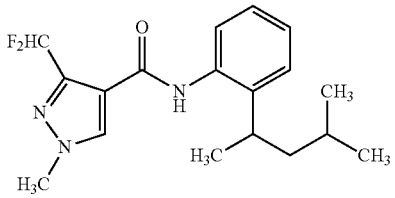 [SMILES: CC(C)CC(C)c1ccccc1NC(=O)c1cn(C)nc1C(F)F]

(6-5) 3-(trifluoromethyl)-N-[2-(1,3-dimethylbutyl)phenyl]-5-fluoro-1-methyl-1H-pyrazole-4-carboxamide (known from WO 2004/067515) of the formula

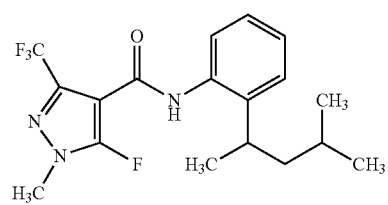 [SMILES: CC(C)CC(C)c1ccccc1NC(=O)c1c(C(F)(F)F)nn(C)c1F]

(6-6) 3-(trifluoromethyl)-N-[2-(1,3-dimethylbutyl)phenyl]-5-chloro-1-methyl-1H-pyrazole-4-carboxamide (known from JP-A 10-251240) of the formula

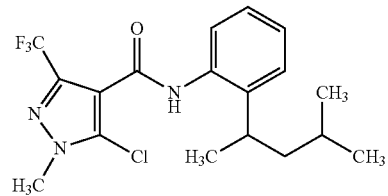 [SMILES: CC(C)CC(C)c1ccccc1NC(=O)c1c(C(F)(F)F)nn(C)c1Cl]

(6-7) 1,3-dimethyl-N-[2-(1,3,3-trimethylbutyl)phenyl]-1H-pyrazole-4-carboxamide of the formula

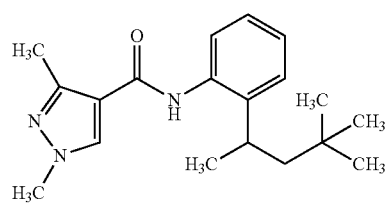

(6-8) 5-fluoro-1,3-dimethyl-N-[2-(1,3,3-trimethylbutyl)phenyl]-1H-pyrazole-4-carboxamide (known from WO 03/010149) of the formula

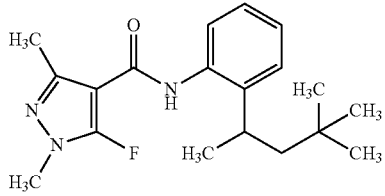

(6-9) 3-(difluoromethyl)-1-methyl-N-[2-(1,3,3-trimethylbutyl)phenyl]-1H-pyrazole-4-carboxamide of the formula

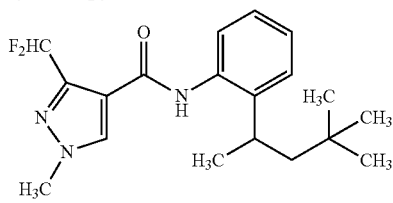 [SMILES: CC(CC(C)(C)C)c1ccccc1NC(=O)c1cn(C)nc1C(F)F]

(6-10) 3-(trifluoromethyl)-1-methyl-N-[2-(1,3,3-trimethylbutyl)phenyl]-1H-pyrazole-4-carboxamide of the formula

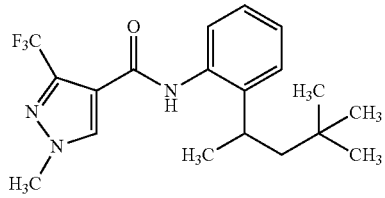 [SMILES: CC(CC(C)(C)C)c1ccccc1NC(=O)c1cn(C)nc1C(F)(F)F]

(6-11) 3-(trifluoromethyl)-5-fluoro-1-methyl-N-[2-(1,3,3-trimethylbutyl)phenyl]-1H-pyrazole-4-carboxamide (known from WO 2004/067515) of the formula

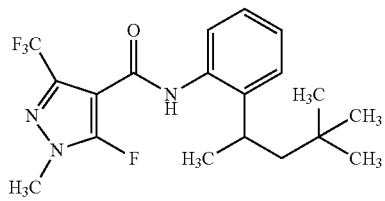 [SMILES: CC(CC(C)(C)C)c1ccccc1NC(=O)c1c(C(F)(F)F)nn(C)c1F]

(6-12) 3-(trifluoromethyl)-5-chloro-1-methyl-N-[2-(1,3,3-trimethylbutyl)phenyl]-1H-pyrazole-4-carboxamide of the formula

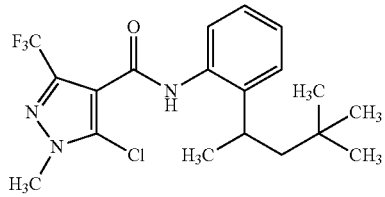

(6-13) N-[2-(1,3-dimethylbutyl)phenyl]-2-iodobenzamide (known from WO 2004/005242) of the formula

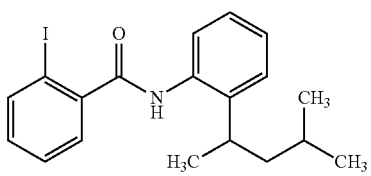 [SMILES: CC(C)CC(C)c1ccccc1NC(=O)c1ccccc1I]

(6-14) 2-iodo-N-[2-(1,3,3-trimethylbutyl)phenyl]benzamide (known from WO 2004/005242) of the formula

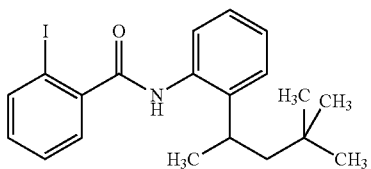 [SMILES: CC(CC(C)(C)C)c1ccccc1NC(=O)c1ccccc1I]

(6-15) N-[2-(1,3-dimethylbutyl)phenyl]-2-(trifluoromethyl)benzamide (known from WO 2004/005242) of the formula

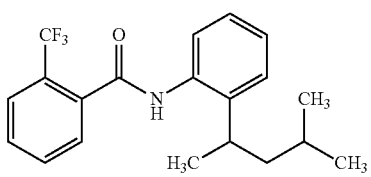 [SMILES: CC(C)CC(C)c1ccccc1NC(=O)c1ccccc1C(F)(F)F]

(6-16) 2-(trifluormethyl)-N-[2-(1,3,3-trimethylbutyl)phenyl]benzamide (known from WO 2004/005242) of the formula

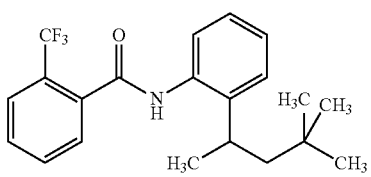 [SMILES: CC(CC(C)(C)C)c1ccccc1NC(=O)c1ccccc1C(F)(F)F]

(6-17) 2-chloro-N-(1,1,3-trimethylindan-4-yl)nicotinamide (known from EP-A 0 256 503) of the formula

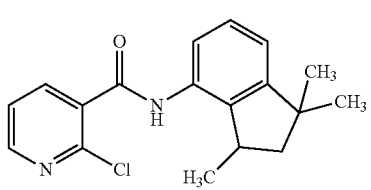 [SMILES: CC1CC(C)(C)c2cccc(NC(=O)c3cccnc3Cl)c21]

(6-18) boscalid (known from DE-A 195 31 813) of the formula

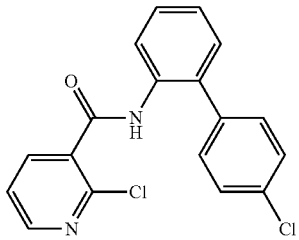 [SMILES: O=C(Nc1ccccc1-c1ccc(Cl)cc1)c1cccnc1Cl]

(6-19) furametpyr (known from EP-A 0 315 502) of the formula

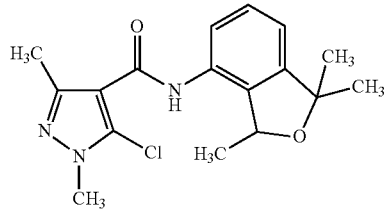

(6-20) N-(3-p-tolylthiophen-2-yl)-1-methyl-3-trifluoromethyl-1H-pyrazole-4-carboxamide (known from EP-A 0 737 682) of the formula

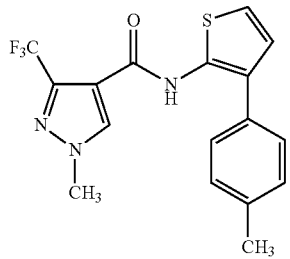 [SMILES: Cc1ccc(-c2ccsc2NC(=O)c2cn(C)nc2C(F)(F)F)cc1]

(6-21) penthiopyrad (known from EP-A 0 737 682) of the formula

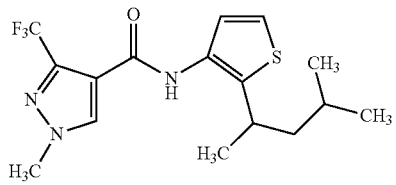 [SMILES: CC(C)CC(C)c1sccc1NC(=O)c1cn(C)nc1C(F)(F)F]

(6-22) N-[2-(1,3-dimethylbutyl)phenyl]-1-methyl-4-(trifluoromethyl)-1H-pyrrole-3-carboxamide (known from WO 02/38542) of the formula

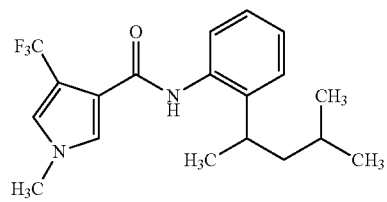 [SMILES: CC(C)CC(C)c1ccccc1NC(=O)c1cn(C)cc1C(F)(F)F]

(6-23) N-(3',4'-dichloro-5-fluoro-1,1'-biphenyl-2-yl)-3-(difluoromethyl)-1-methyl-1H-pyrazole-4-carboxamide (known from WO 03/070705) of the formula

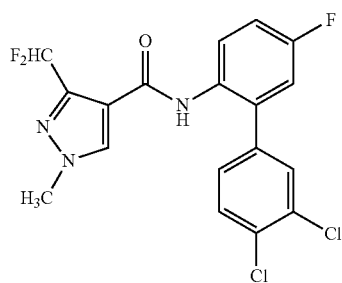 [SMILES: Cn1cc(C(=O)Nc2ccc(F)cc2-c2ccc(Cl)c(Cl)c2)c(C(F)F)n1]

(6-24) 3-(difluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

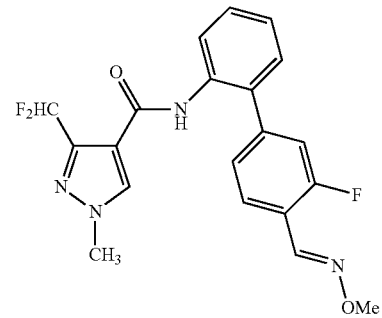 [SMILES: CO/N=C/c1ccc(-c2ccccc2NC(=O)c2cn(C)nc2C(F)F)cc1F]

(6-25) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

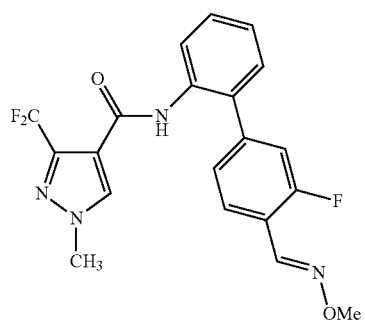

(6-26) N-(3',4'-dichloro-1,1'-biphenyl-2-yl)-5-fluoro-1,3-dimethyl-1H-pyrazole-4-carboxamide (known from WO 00/14701) of the formula

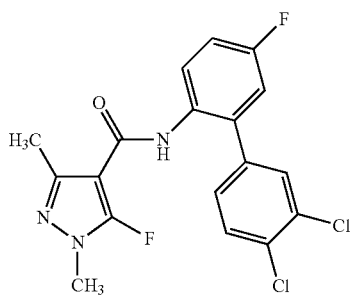 [SMILES: Cc1nn(C)c(F)c1C(=O)Nc1ccc(F)cc1-c1ccc(Cl)c(Cl)c1]

(6-27) N-(4'-chloro-3'-fluoro-1,1'-biphenyl-2-yl)-2-methyl-4-(trifluoromethyl)-1,3-thiazole-5-carboxamide (known from WO 03/066609) of the formula

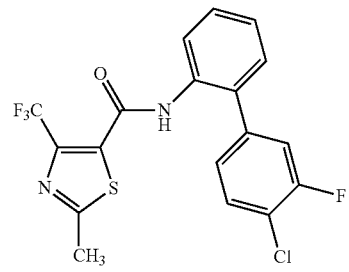 [SMILES: Cc1nc(C(F)(F)F)c(C(=O)Nc2ccccc2-c2ccc(Cl)c(F)c2)s1]

(6-28) N-(4'-chloro-1,1'-biphenyl-2-yl)-4-(difluoromethyl)-2-methyl-1,3-thiazole-5-carboxamide (known from WO 03/066610) of the formula

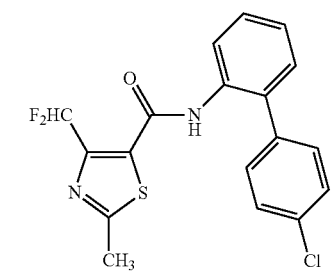 [SMILES: Cc1nc(C(F)F)c(C(=O)Nc2ccccc2-c2ccc(Cl)cc2)s1]

(6-29) N-(4'-bromo-1,1'-biphenyl-2-yl)-4-(difluoromethyl)-2-methyl-1,3-thiazole-5-carboxamide (known from WO 03/066610) of the formula

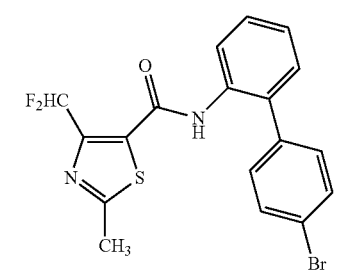 [SMILES: Cc1nc(C(F)F)c(C(=O)Nc2ccccc2-c2ccc(Br)cc2)s1]

(6-30) 4-(difluoromethyl)-2-methyl-N-[4'-(trifluoromethyl)-1,1'-biphenyl-2-yl]-1,3-thiazole-5-carboxamide (known from WO 03/066610) of the formula

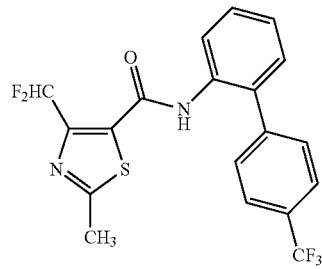 [SMILES: Cc1nc(C(F)F)c(C(=O)Nc2ccccc2-c2ccc(C(F)(F)F)cc2)s1]

(6-31) N-(4'-iodo-1,1'-biphenyl-2-yl)-4-(difluoromethyl)-2-methyl-1,3-thiazole-5-carboxamide (known from WO 03/066610) of the formula

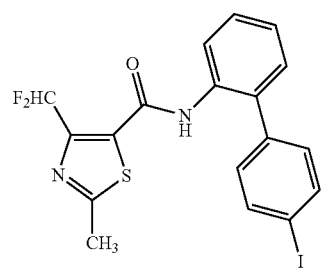 [SMILES: Cc1nc(C(F)F)c(C(=O)Nc2ccccc2-c2ccc(I)cc2)s1]

(6-32) N-(4'-chloro-3'-fluoro-1,1'-biphenyl-2-yl)-2-methyl-4-(difluoromethyl)-1,3-thiazole-5-carboxamide (known from WO 03/066610) of the formula

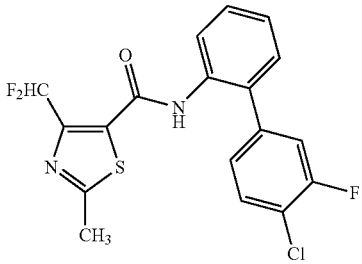 [SMILES: Cc1nc(C(F)F)c(C(=O)Nc2ccccc2-c2ccc(Cl)c(F)c2)s1]

(6-33) ethaboxam (known from EP-A 0 639 574) of the formula

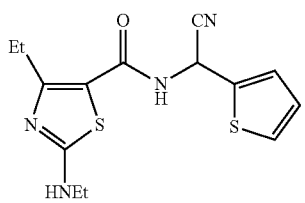

(6-34) fenhexamid (known from EP-A 0 339 418) of the formula

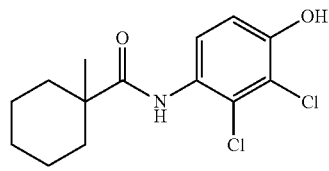 [SMILES: CC1(C(=O)Nc2ccc(O)c(Cl)c2Cl)CCCCC1]

(6-35) carpropamid (known from EP-A 0 341 475) of the formula

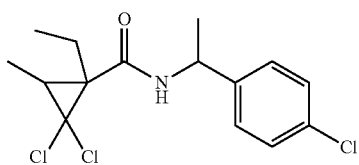 [SMILES: CCC1(C(=O)NC(C)c2ccc(Cl)cc2)C(C)C1(Cl)Cl]

(6-36) 2-chloro-4-(2-fluoro-2-methylpropionylamino)-N,N-dimethylbenzamide (known from EP-A 0 600 629) of the formula

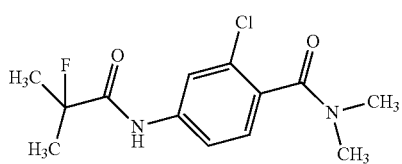 [SMILES: CN(C)C(=O)c1ccc(NC(=O)C(C)(C)F)cc1Cl]

(6-37) fluopicolide (known from WO 99/42447) of the formula

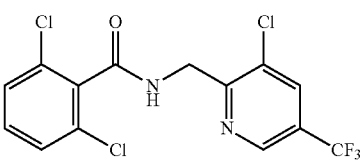 [SMILES: O=C(NCc1ncc(C(F)(F)F)cc1Cl)c1c(Cl)cccc1Cl]

(6-38) zoxamide (known from EP-A 0 604 019) of the formula

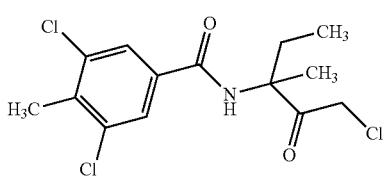 [SMILES: CCC(C)(NC(=O)c1cc(Cl)c(C)c(Cl)c1)C(=O)CCl]

(6-39) 3,4-dichloro-N-(2-cyanophenyl)isothiazole-5-carboxamide (known from WO 99/24413) of the formula

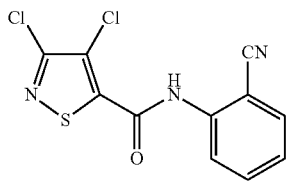 [SMILES: N#Cc1ccccc1NC(=O)c1snc(Cl)c1Cl]

(6-40) carboxin (known from U.S. Pat. No. 3,249,499) of the formula

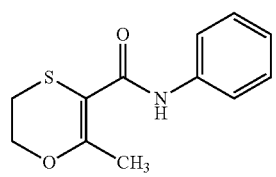 [SMILES: CC1=C(C(=O)Nc2ccccc2)SCCO1]

(6-41) tiadinil (known from U.S. Pat. No. 6,616,054) of the formula

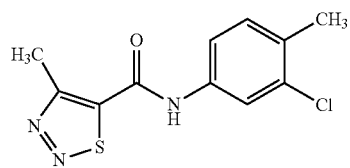 [SMILES: Cc1ccc(NC(=O)c2snnc2C)cc1Cl]

(6-42) silthiofam (known from WO 96/18631) of the formula

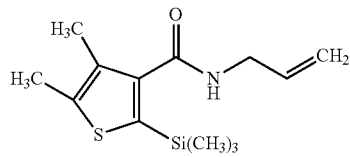

(6-43) N-[2-(1,3-dimethylbutyl)phenyl]-1-methyl-4-(trifluoromethyl)-1H-pyrrole-3-carboxamide (known from WO 02/38542) of the formula

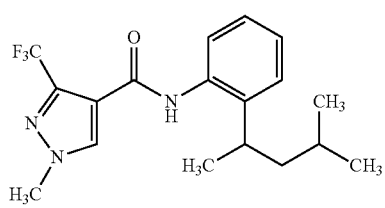 [SMILES: CC(C)CC(C)c1ccccc1NC(=O)c1cn(C)nc1C(F)(F)F]

(6-44) N-{2-[3-chloro-5-(trifluoromethyl)pyridin-2-yl]ethyl}-2-(trifluoromethyl)benzamide (known from WO 2004/016088) of the formula

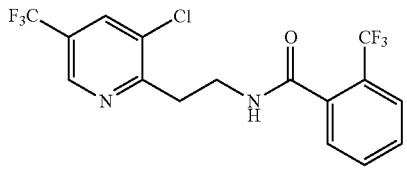 [SMILES: O=C(NCCc1ncc(C(F)(F)F)cc1Cl)c1ccccc1C(F)(F)F]

(6-45) N-(2-bicyclopropyl-2-yl-phenyl)-1-methyl-3-trifluoromethyl-1H-pyrazole-4-carboxamide (known from WO 2006/015865) of the formula

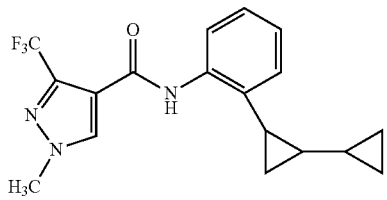 [SMILES: Cn1cc(C(=O)Nc2ccccc2C2CC2C2CC2)c(C(F)(F)F)n1]

(6-46) N-(2-bicyclopropyl-2-yl-phenyl)-1-methyl-3-difluoromethyl-1H-pyrazole-4-carboxamide (known from WO 2006/015865) of the formula

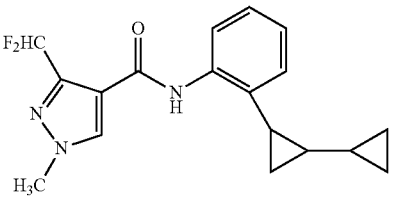 [SMILES: Cn1cc(C(=O)Nc2ccccc2C2CC2C2CC2)c(C(F)F)n1]

(6-47) N-[2-(1'-methylbicyclopropyl-2-yl)phenyl]-1-methyl-3-trifluoromethyl-1H-pyrazole-4-carboxamide (known from WO 2006/015865) of the formula

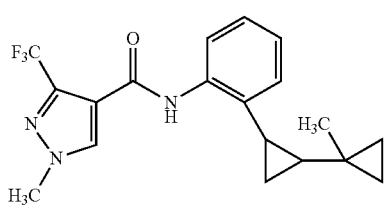 [SMILES: Cn1cc(C(=O)Nc2ccccc2C2CC2C2(C)CC2)c(C(F)(F)F)n1]

(6-48) N-[2-(1'-methylbicyclopropyl-2-yl)phenyl]-1-methyl-3-difluoromethyl-1H-pyrazole-4-carboxamide (known from WO 2006/015865) of the formula

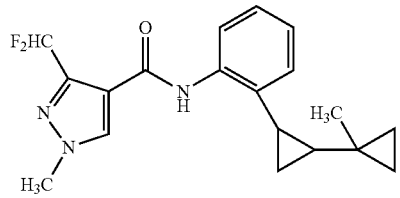 [SMILES: Cn1cc(C(=O)Nc2ccccc2C2CC2C2(C)CC2)c(C(F)F)n1]

(6-49) N-[1-(5-bromo-3-chloropyridin-2-yl)ethyl]-2,4-dichloronicotinamide of the formula

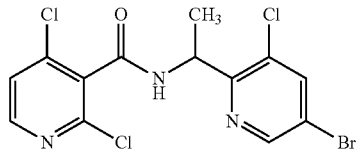 [SMILES: CC(NC(=O)c1c(Cl)ccnc1Cl)c1ncc(Br)cc1Cl]

(6-50) N-(5-bromo-3-chloropyridin-2-yl)methyl-2,4-dichloronicotinamide of the formula

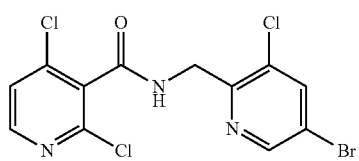 [SMILES: O=C(NCc1ncc(Br)cc1Cl)c1c(Cl)ccnc1Cl]

(6-51) N-(3',4'-dichloro-5-fluoro-1,1'-biphenyl-2-yl)-3-(difluoromethyl)-1-methyl-1H-pyrazole-4-carboxamide (known from WO 2005/123690) of the formula

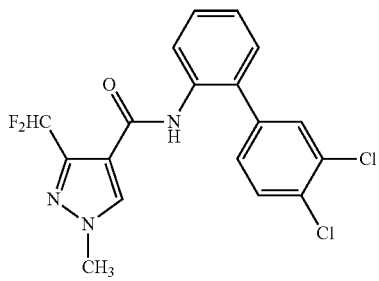 [SMILES: Cn1cc(C(=O)Nc2ccccc2-c2ccc(Cl)c(Cl)c2)c(C(F)F)n1]

(6-52) N-(3',4'-dichloro-5-fluoro-1,1'-biphenyl-2-yl)-3-(difluoromethyl)-1-methyl-1H-pyrazole-4-carboxamide (known from WO 2005/123689) of the formula

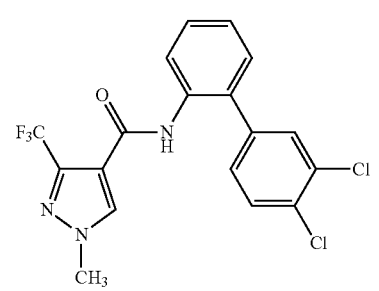 [SMILES: Cn1cc(C(=O)Nc2ccccc2-c2ccc(Cl)c(Cl)c2)c(C(F)(F)F)n1]

(6-53) 3-difluoromethyl-1-methyl-1H-pyrazole-4-carboxylic acid [2-(3,3-dimethyl-butyl)-phenyl]-amide of the formula

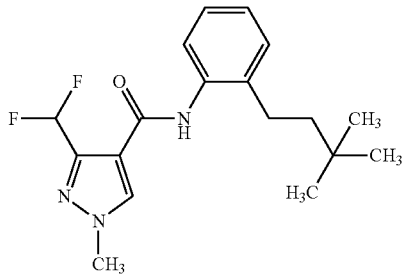 [SMILES: Cn1cc(C(=O)Nc2ccccc2CCC(C)(C)C)c(C(F)F)n1]

Group (7) dithiocarbamates selected from (7-1) mancozeb (known from DE-A 12 34 704) having the IUPAC name manganese ethylenebis(dithiocarbamate) (polymeric) complex with zinc salt (7-2) maneb (known from U.S. Pat. No. 2,504,404) of the formula

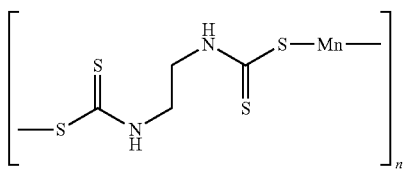

(7-3) metiram (known from DE-A 10 76 434) having the IUPAC name zinc ammoniate ethylenebis(dithiocarbamate)-poly(ethylenethiuram disulphide)

(7-4) propineb (known from GB 935 981) of the formula

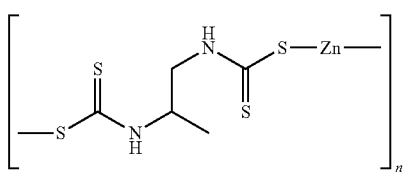

(7-5) thiram (known from U.S. Pat. No. 1,972,961) of the formula

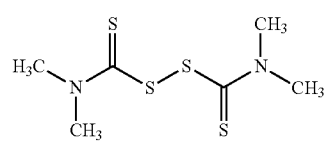

(7-6) zineb (known from DE-A 10 81 446) of the formula

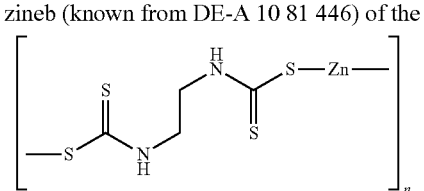

(7-7) ziram (known from U.S. Pat. No. 2,588,428) of the formula

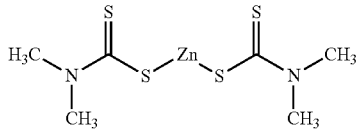

Group (8) acylalanines selected from (8-1) benalaxyl (known from DE-A 29 03 612) of the formula

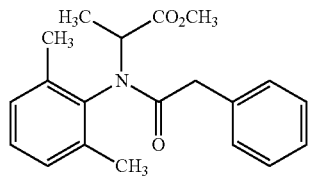 [SMILES: COC(=O)C(C)N(C(=O)Cc1ccccc1)c1c(C)cccc1C]

(8-2) furalaxyl (known from DE-A 25 13 732) of the formula

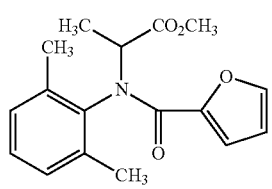 [SMILES: COC(=O)C(C)N(C(=O)c1ccco1)c1c(C)cccc1C]

(8-3) metalaxyl (known from DE-A 25 15 091) of the formula

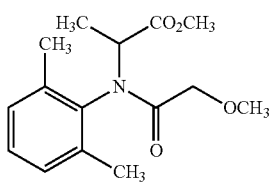 [SMILES: COCC(=O)N(c1c(C)cccc1C)C(C)C(=O)OC]

(8-4) metalaxyl-M (known from WO 96/01559) of the formula

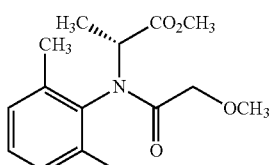

(8-5) benalaxyl-M of the formula

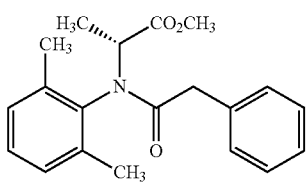 [SMILES: COC(=O)[C@@H](C)N(C(=O)Cc1ccccc1)c1c(C)cccc1C]

Group (9): anilinopyrimidines selected from (9-1) cyprodinil (known from EP-A 0 310 550) of the formula

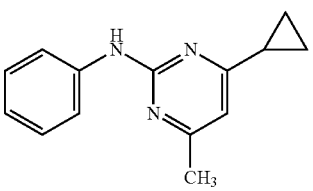

(9-2) mepanipyrim (known from EP-A 0 270 111) of the formula

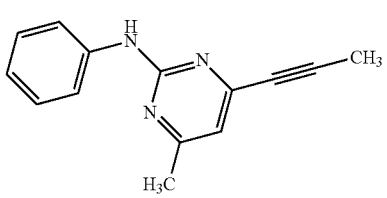 [SMILES: CC#Cc1cc(C)nc(Nc2ccccc2)n1]

(9-3) pyrimethanil (known from DD 151 404) of the formula

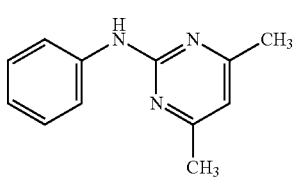

Group (10): benzimidazoles selected from (10-1) 6-chloro-5-[(3,5-dimethylisoxazol-4-yl)sulphonyl]-2,2-difluoro-5H-[1,3]dioxolo[4,5-f]-benzimidazole (known from WO 97/06171) of the formula

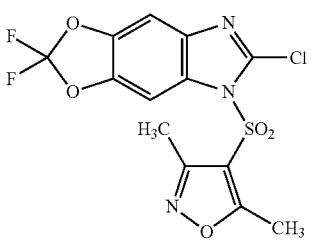 [SMILES: Cc1noc(C)c1S(=O)(=O)n1c(Cl)nc2cc3c(cc21)OC(F)(F)O3]

(10-2) benomyl (known from U.S. Pat. No. 3,631,176) of the formula

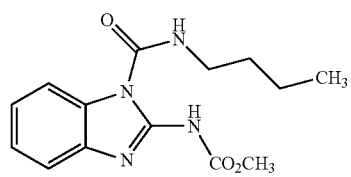 [SMILES: CCCCNC(=O)n1c(NC(=O)OC)nc2ccccc21]

(10-3) carbendazim (known from U.S. Pat. No. 3,010,968) of the formula

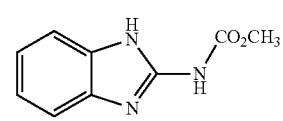 [SMILES: COC(=O)Nc1nc2ccccc2[nH]1]

(10-4) chlorfenazole of the formula

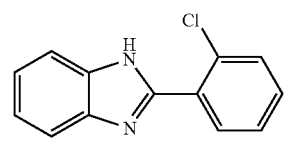

(10-5) fuberidazole (known from DE-A 12 09 799) of the formula

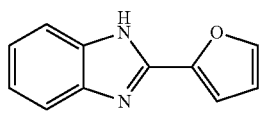 [SMILES: c1coc(-c2nc3ccccc3[nH]2)c1]

(10-6) thiabendazole (known from U.S. Pat. No. 3,206,468) of the formula

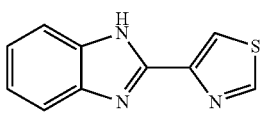 [SMILES: c1ccc2[nH]c(-c3cscn3)nc2c1]

Group (11): carbamates selected from (11-1) diethofencarb (known from EP-A 0 078 663) of the formula

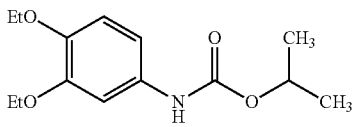

(11-2) propamocarb (known from U.S. Pat. No. 3,513,241) of the formula

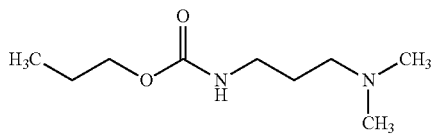

(11-3) propamocarb hydrochloride (known from U.S. Pat. No. 3,513,241) of the formula

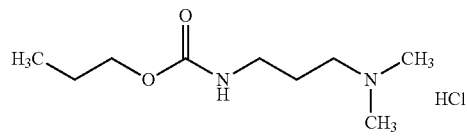

(11-4) propamocarb-fosetyl of the formula

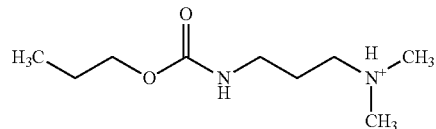
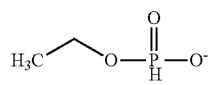

Group (12): dicarboximides selected from
(12-1) captafol (known from U.S. Pat. No. 3,178,447) of the formula

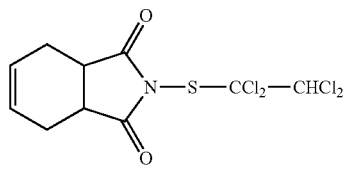

(12-2) captan (known from U.S. Pat. No. 2,553,770) of the formula

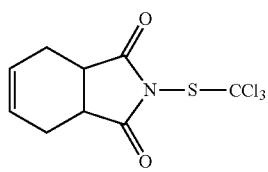

(12-3) folpet (known from U.S. Pat. No. 2,553,770) of the formula

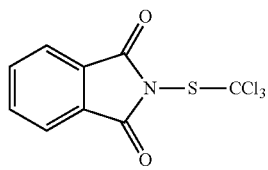

(12-4) iprodione (known from DE-A 21 49 923) of the formula

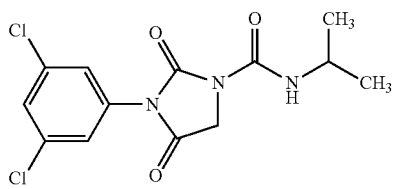 [SMILES: CC(C)NC(=O)N1CC(=O)N(c2cc(Cl)cc(Cl)c2)C1=O]

(12-5) procymidone (known from DE-A 20 12 656) of the formula

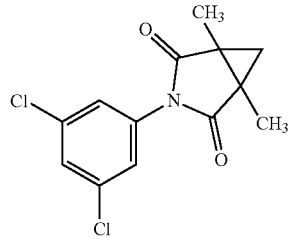 [SMILES: CC12CC1(C)C(=O)N(c1cc(Cl)cc(Cl)c1)C2=O]

(12-6) vinclozolin (known from DE-A 22 07 576) of the formula

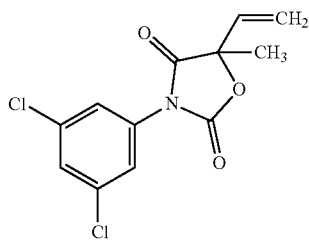 [SMILES: C=CC1(C)OC(=O)N(c2cc(Cl)cc(Cl)c2)C1=O]

Group (13): guanidines selected from
(13-1) dodine (known from GB 11 03 989) of the formula

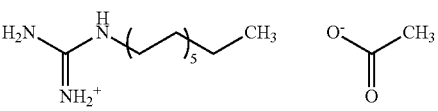

(13-2) guazatine (known from GB 11 14 155)
(13-3) iminoctadine triacetate (known from EP-A 0 155 509) of the formula

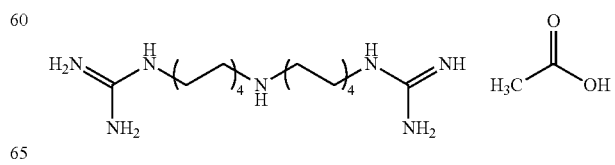

(13-4) iminoctadine tris(albesilate)

Group (14): imidazoles selected from
(14-1) cyazofamid (known from EP-A 0 298 196) of the formula

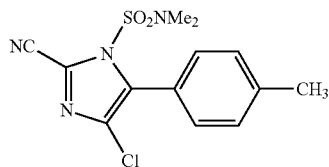

(14-2) prochloraz (known from DE-A 24 29 523) of the formula

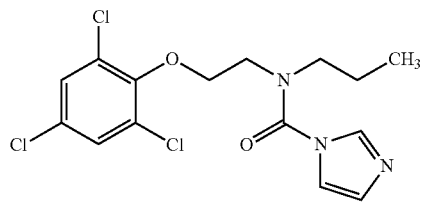 [SMILES: CCCN(CCOc1c(Cl)cc(Cl)cc1Cl)C(=O)n1ccnc1]

(14-3) triazoxide (known from DE-A 28 02 488) of the formula

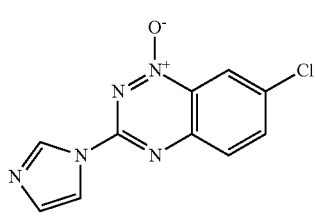 [SMILES: [O-][n+]1nc(-n2ccnc2)nc2ccc(Cl)cc21]

(14-4) pefurazoate (known from EP-A 0 248 086) of the formula

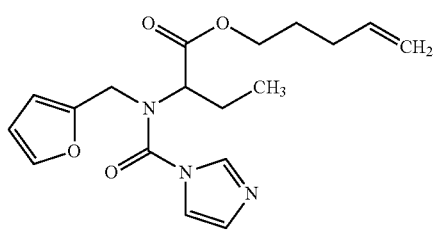 [SMILES: C=CCCCOC(=O)C(CC)N(Cc1ccco1)C(=O)n1ccnc1]

Group (15): morpholines selected from
(15-1) aldimorph (known from DD 140 041) of the formula

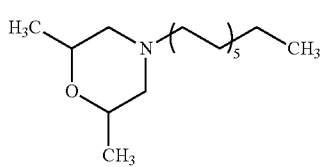

(15-2) tridemorph (known from GB 988 630) of the formula

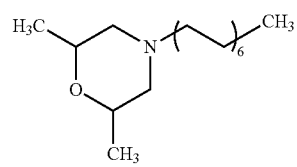

(15-3) dodemorph (known from DE-A 25 432 79) of the formula

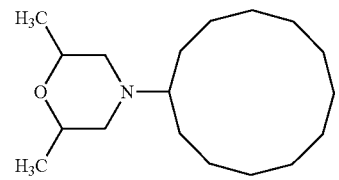 [SMILES: CC1CN(C2CCCCCCCCCCC2)CC(C)O1]

(15-4) fenpropimorph (known from DE-A 26 56 747) of the formula

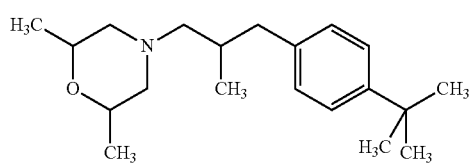 [SMILES: CC(Cc1ccc(C(C)(C)C)cc1)CN1CC(C)OC(C)C1]

(15-5) dimethomorph (known from EP-A 0 219 756) of the formula

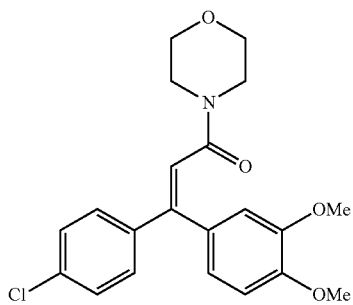 [SMILES: COc1ccc(/C(=C\C(=O)N2CCOCC2)c2ccc(Cl)cc2)cc1OC]

(15-6) flumorph (known from EP-A 0 086 438) of the formula

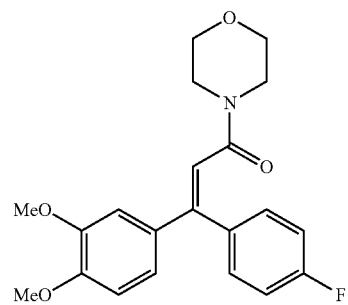 [SMILES: COc1ccc(/C(=C/C(=O)N2CCOCC2)c2ccc(F)cc2)cc1OC]

Group (16): pyrroles selected from (16-1) fenpiclonil (known from EP-A 0 236 272) of the formula

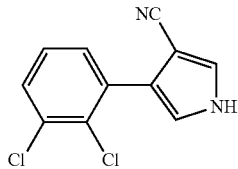 [SMILES: N#Cc1c[nH]cc1-c1cccc(Cl)c1Cl]

(16-2) fludioxonil (known from EP-A 0 206 999) of the formula

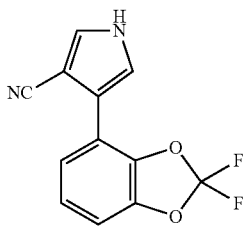 [SMILES: N#Cc1c[nH]cc1-c1cccc2c1OC(F)(F)O2]

(16-3) pyrrolnitrin (known from JP-A 65-25876) of the formula

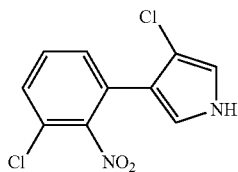 [SMILES: O=[N+]([O-])c1c(Cl)cccc1-c1c[nH]cc1Cl]

Group (17): phosphonates selected from (17-1) fosetyl-Al (known from DE-A 24 56 627) of the formula

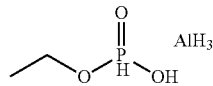

(17-2) phosphonic acid (known chemical) of the formula

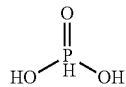

Group (18): phenylethanamides (known from WO 96/23793, E or Z isomer, preferably E isomer) selected from (18-1) 2-(2,3-dihydro-1H-inden-5-yl)-N-[2-(3,4-dimethoxyphenyl)ethyl]-2-(methoxyimino)-acetamide of the formula

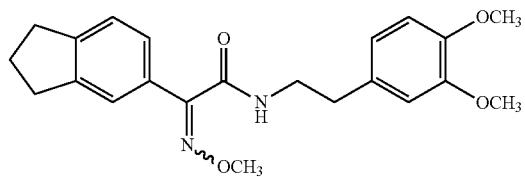

(18-2) N-[2-(3,4-dimethoxyphenyl)ethyl]-2-(methoxyimino)-2-(5,6,7,8-tetrahydronaphthalen-2-yl)acetamide of the formula

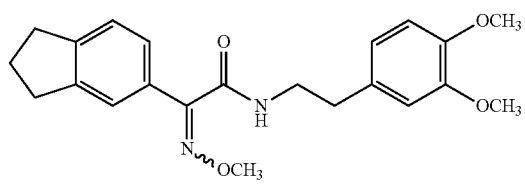 [SMILES: CON=C(C(=O)NCCc1ccc(OC)c(OC)c1)c1ccc2c(c1)CCC2]

(18-3) 2-(4-chlorophenyl)-N-[2-(3,4-dimethoxyphenyl)ethyl]-2-(methoxyimino)acetamide of the formula

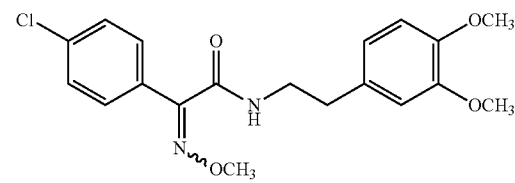 [SMILES: CON=C(C(=O)NCCc1ccc(OC)c(OC)c1)c1ccc(Cl)cc1]

(18-4) 2-(4-bromophenyl)-N-[2-(3,4-dimethoxyphenyl)ethyl]-2-(methoxyimino)acetamide of the formula

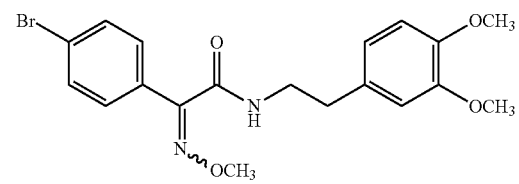

(18-5) 2-(4-methylphenyl)-N-[2-(3,4-dimethoxyphenyl)ethyl]-2-(methoxyimino)acetamide of the formula

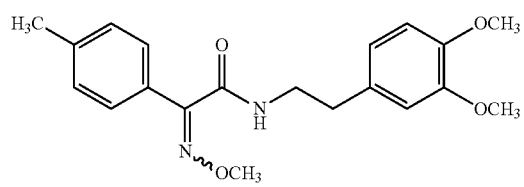 [SMILES: CON=C(C(=O)NCCc1ccc(OC)c(OC)c1)c1ccc(C)cc1]

(18-6) 2-(4-ethylphenyl)-N-[2-(3,4-dimethoxyphenyl)ethyl]-2-(methoxyimino)acetamide of the formula

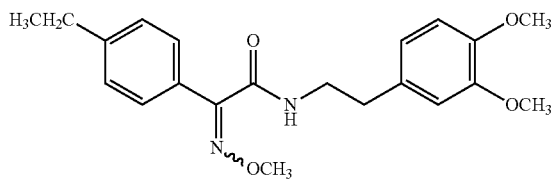

Group (19): fungicides selected from
(19-1) acibenzolar-S-methyl (known from EP-A 0 313 512) of the formula

(19-2) chlorothalonil (known from U.S. Pat. No. 3,290,353) of the formula

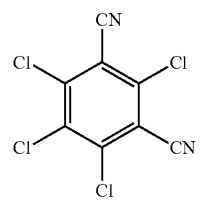 [SMILES: N#Cc1c(Cl)c(Cl)c(Cl)c(C#N)c1Cl]

(19-3) cymoxanil (known from DE-A 23 12 956) of the formula

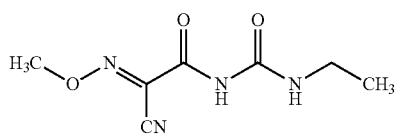

(19-4) edifenphos (known from DE-A 14 93 736) of the formula

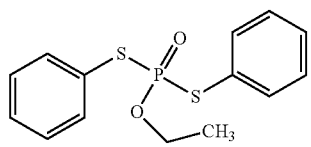 [SMILES: CCOP(=O)(Sc1ccccc1)Sc1ccccc1]

(19-5) famoxadone (known from EP-A 0 393 911) of the formula

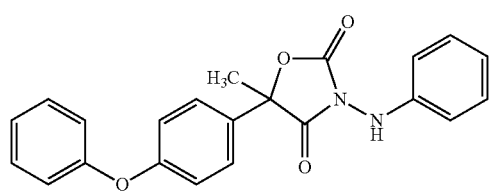 [SMILES: CC1(c2ccc(Oc3ccccc3)cc2)OC(=O)N(Nc2ccccc2)C1=O]

(19-6) fluazinam (known from EP-A 0 031 257) of the formula

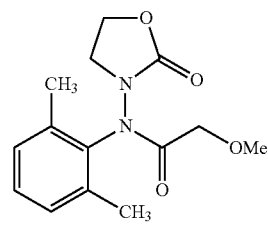 [SMILES: COCC(=O)N(c1c(C)cccc1C)N1CCOC1=O]

(19-7) copper oxychloride
(19-8) copper hydroxide
(19-9) oxadixyl (known from DE-A 30 30 026) of the formula

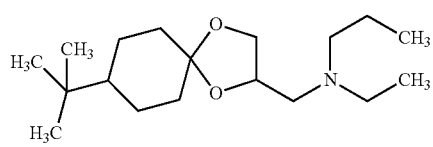 [SMILES: CCCN(CC)CC1COC2(CCC(C(C)(C)C)CC2)O1]

(19-10) spiroxamine (known from DE-A 37 35 555) of the formula

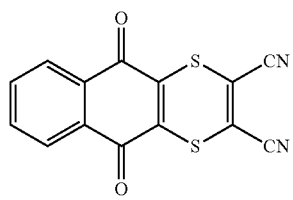 [SMILES: N#Cc1sc2c(=O)c3ccccc3c(=O)c=2sc1C#N]

(19-11) dithianon (known from JP-A 44-29464) of the formula

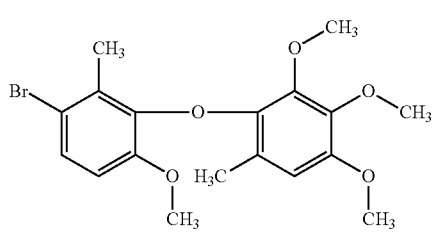 [SMILES: COc1ccc(Br)c(C)c1Oc1c(C)cc(OC)c(OC)c1OC]

(19-12) metrafenone (known from EP-A 0 897 904) of the formula (19-13) fenamidone (known from EP-A 0 629 616) of the formula

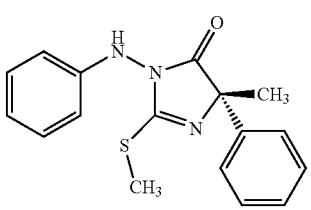 [SMILES: CSC1=N[C@@](C)(c2ccccc2)C(=O)N1Nc1ccccc1]

(19-14) 2,3-dibutyl-6-chlorothieno[2,3-d]pyrimidin-4(3H)-one (known from WO 99/14202) of the formula

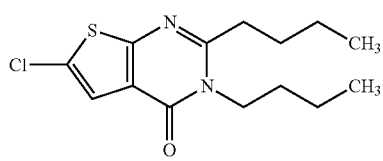 [SMILES: CCCCc1nc2sc(Cl)cc2c(=O)n1CCCC]

(19-15) probenazole (known from U.S. Pat. No. 3,629,428) of the formula

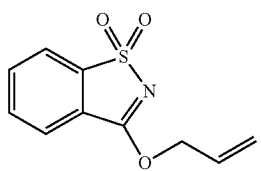

(19-16) isoprothiolane (known from U.S. Pat. No. 3,856,814) of the formula

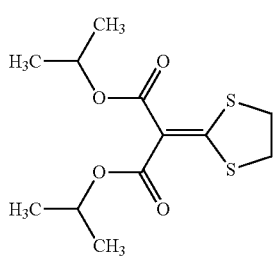 [SMILES: CC(C)OC(=O)C(C(=O)OC(C)C)=C1SCCS1]

(19-17) kasugamycin (known from GB 1 094 567) of the formula

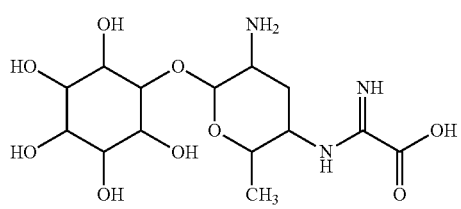 [SMILES: CC1OC(OC2C(O)C(O)C(O)C(O)C2O)C(N)CC1NC(=N)C(=O)O]

(19-18) phthalide (known from JP-A 57-55844) of the formula (19-19) ferimzone (known from EP-A 0 019 450) of the formula

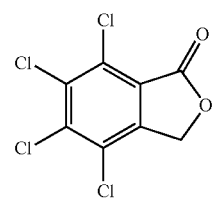 [SMILES: O=C1OCc2c(Cl)c(Cl)c(Cl)c(Cl)c21]

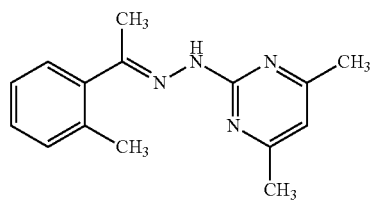 [SMILES: C/C(=N\Nc1nc(C)cc(C)n1)c1ccccc1C]

(19-20) tricyclazole (known from DE-A 22 50 077) of the formula

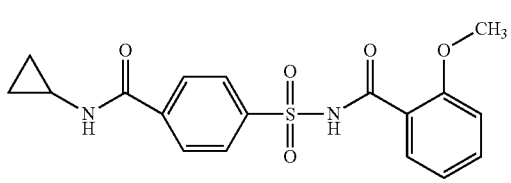 [SMILES: COc1ccccc1C(=O)NS(=O)(=O)c1ccc(C(=O)NC2CC2)cc1]

(19-21) N-({4-[(cyclopropylamino)carbonyl]phenyl}sulphonyl)-2-methoxybenzamide of the formula (19-22) 2-(4-chlorophenyl)-N-{2-[3-methoxy-4-(prop-2-yn-1-yloxy)phenyl]ethyl}-2-(prop-2-yn-1-yloxy)acetamide (known from WO 01/87822) of the formula

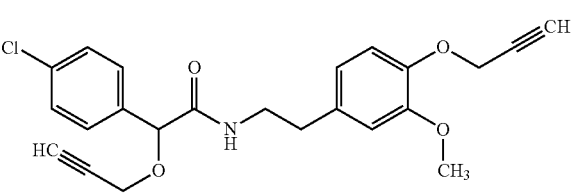 [SMILES: C#CCOc1ccc(CCNC(=O)C(OCC#C)c2ccc(Cl)cc2)cc1OC]

(19-23) proquinazid (known from WO 09426722) of the formula

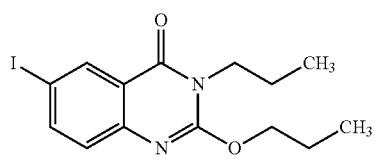 [SMILES: CCCOc1nc2ccc(I)cc2c(=O)n1CCC]

(19-24) quinoxyfen (known from EP-A 0 326 330) of the formula

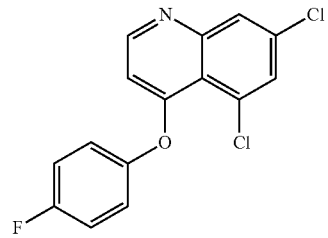 [SMILES: Fc1ccc(Oc2ccnc3cc(Cl)cc(Cl)c23)cc1]

(19-25) cyflufenamid (known from WO 96/19442) of the formula

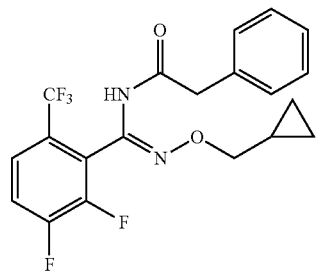 [SMILES: O=C(Cc1ccccc1)N/C(=N\OCC1CC1)c1c(C(F)(F)F)ccc(F)c1F]

(19-26) pyribencarb (known from WO 01/10825) of the formula

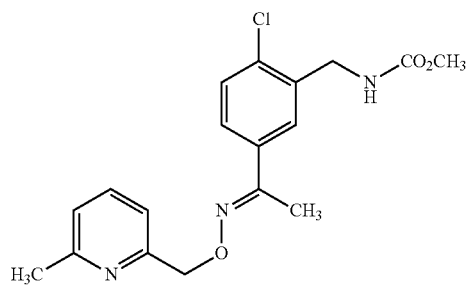 [SMILES: COC(=O)NCc1cc(/C(C)=N/OCc2cccc(C)n2)ccc1Cl]

(19-27) 3-[5-(4-chlorophenyl)-2,3-dimethyl-3-isoxazolidinyl]pyridine (known from EP-A 1 035 122) of the formula

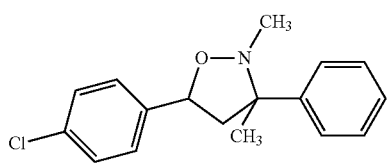 [SMILES: CN1OC(c2ccc(Cl)cc2)CC1(C)c1ccccc1]

Group (20): (thio)urea derivatives selected from
(20-1) pencycuron (known from DE-A 27 32 257) of the formula

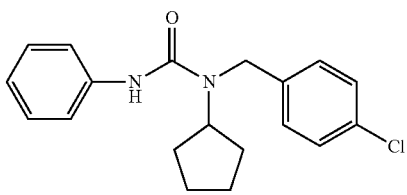 [SMILES: O=C(Nc1ccccc1)N(Cc1ccc(Cl)cc1)C1CCCC1]

(20-2) thiophanate-methyl (known from DE-A 18 06 123) of the formula

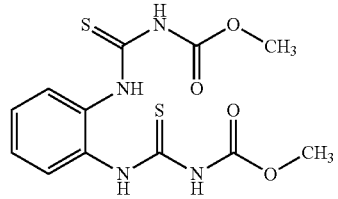 [SMILES: COC(=O)NC(=S)Nc1ccccc1NC(=S)NC(=O)OC]

(20-3) thiophanate-ethyl (known from DE-A 18 06 123) of the formula

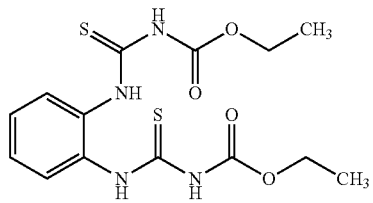 [SMILES: CCOC(=O)NC(=S)Nc1ccccc1NC(=S)NC(=O)OCC]

Group (21): amides selected from
(21-1) fenoxanil (known from EP-A 0 262 393) of the formula

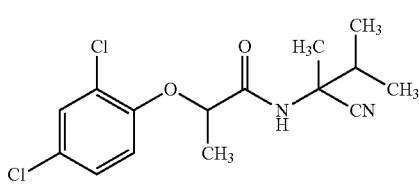 [SMILES: CC(Oc1ccc(Cl)cc1Cl)C(=O)NC(C)(C#N)C(C)C]

(21-2) diclocymet (known from JP-A 7-206608) of the formula

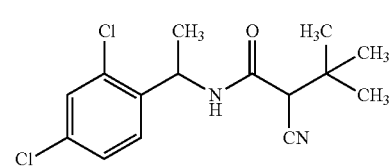 [SMILES: CC(NC(=O)C(C#N)C(C)(C)C)c1ccc(Cl)cc1Cl]

Group (22): triazolopyrimidines selected from
(22-1) 5-chloro-N-[(1S)-2,2,2-trifluoro-1-methylethyl]-6-(2,4,6-trifluorophenyl)[1,2,4]triazolo-[1,5-a]pyrimidine-7-amine (known from U.S. Pat. No. 5,986,135) of the formula

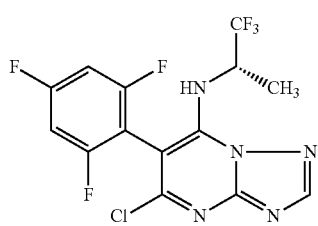 [SMILES: C[C@H](Nc1c(-c2c(F)cc(F)cc2F)c(Cl)nc2ncnn12)C(F)(F)F]

(22-2) 5-chloro-N-[(1R)-1,2-dimethylpropyl]-6-(2,4,6-trifluorophenyl)[1,2,4]triazolo[1,5-a]pyrimidine-7-amine (known from WO 02/38565) of the formula

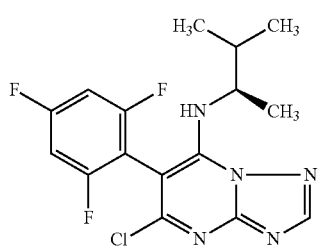 [SMILES: CC(C)[C@@H](C)Nc1c(-c2c(F)cc(F)cc2F)c(Cl)nc2ncnn12]

(22-3) 5-chloro-6-(2-chloro-6-fluorophenyl)-7-(4-methylpiperidin-1-yl)[1,2,4]triazolo[1,5-a]pyrimidine (known from U.S. Pat. No. 5,593,996) of the formula

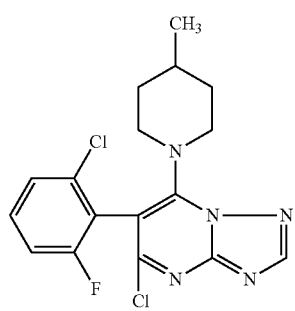 [SMILES: CC1CCN(c2c(-c3c(F)cccc3Cl)c(Cl)nc3ncnn23)CC1]

(22-4) 5-chloro-6-(2,4,6-trifluorophenyl)-7-(4-methylpiperidin-1-yl)[1,2,4]triazolo[1,5-a]pyrimidine (known from DE-A 101 24 208) of the formula

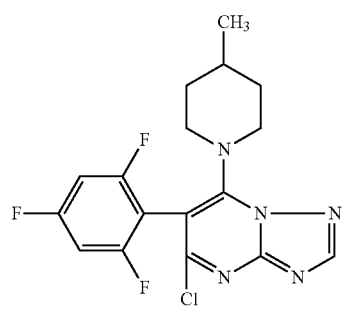 [SMILES: CC1CCN(c2c(-c3c(F)cc(F)cc3F)c(Cl)nc3ncnn23)CC1]

Group (23): iodochromones selected from
(23-1) 2-butoxy-6-iodo-3-propylbenzopyran-4-one (known from WO 03/014103) of the formula

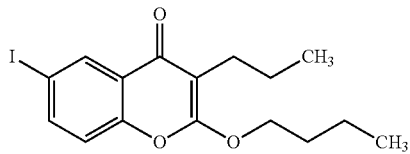 [SMILES: CCCCOc1oc2ccc(I)cc2c(=O)c1CCC]

(23-2) 2-ethoxy-6-iodo-3-propylbenzopyran-4-one (known from WO 03/014103) of the formula

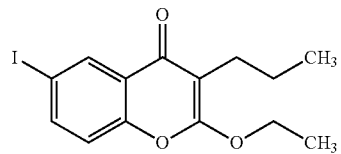 [SMILES: CCCc1c(OCC)oc2ccc(I)cc2c1=O]

(23-3) 6-iodo-2-propoxy-3-propylbenzopyran-4-one (known from WO 03/014103) of the formula

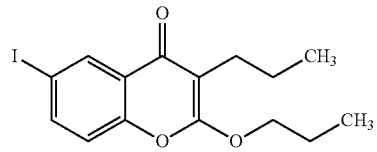 [SMILES: CCCOc1oc2ccc(I)cc2c(=O)c1CCC]

(23-4) 2-but-2-ynyloxy-6-iodo-3-propylbenzopyran-4-one (known from WO 03/014103) of the formula

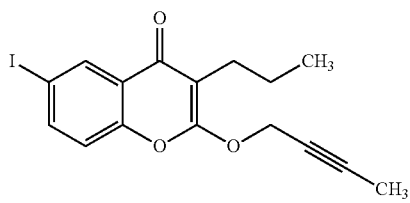 [SMILES: CC#CCOc1oc2ccc(I)cc2c(=O)c1CCC]

(23-5) 6-iodo-2-(1-methylbutoxy)-3-propylbenzopyran-4-one (known from WO 03/014103) of the formula

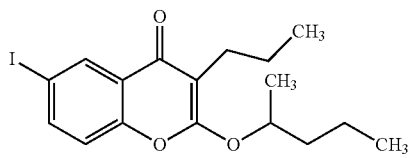 [SMILES: CCCc1c(OC(C)CCC)oc2ccc(I)cc2c1=O]

(23-6) 2-but-3-enyloxy-6-iodobenzopyran-4-one (known from WO 03/014103) of the formula

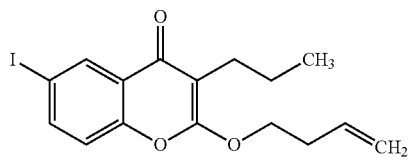 [SMILES: C=CCCOc1oc2ccc(I)cc2c(=O)c1CCC]

(23-7) 3-butyl-6-iodo-2-isopropoxybenzopyran-4-one (known from WO 03/014103) of the formula

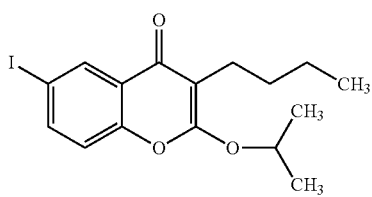 [SMILES: CCCCc1c(OC(C)C)oc2ccc(I)cc2c1=O]

Surprisingly, the fungicidal activity of the active compound combinations according to the invention is substantially higher than the sum of the activities of the individual active compounds. Thus, an unforeseeable true synergistic effect is present, and not just an addition of activities.

The compound (6-35) carpropamid has three asymmetrically substituted carbon atoms. Accordingly, the compound (6-35) can be present as a mixture of different isomers or else in the form of a single component. Particular preference is given to the compounds (1S,3R)-2,2-dichloro-N-[(1R)-1-(4-chlorophenyl)ethyl]-1-ethyl-3-methylcyclopropanecarboxamide of the formula

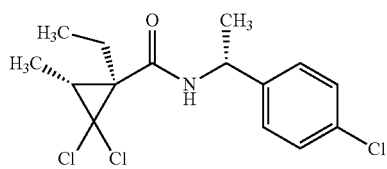 [SMILES: CC[C@@]1(C(=O)N[C@H](C)c2ccc(Cl)cc2)[C@@H](C)C1(Cl)Cl]

and
(1R,3S)-2,2-dichloro-N-[(1R)-1-(4-chlorophenyl)ethyl]-1-ethyl-3-methylcyclopropanecarboxamide of the formula

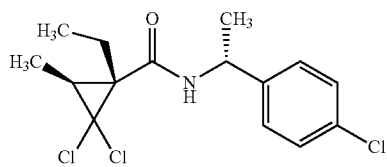 [SMILES: CC[C@]1(C(=O)N[C@H](C)c2ccc(Cl)cc2)[C@H](C)C1(Cl)Cl]

Emphasis is given to active compound combinations according to the invention which, in addition to (1-1) glyphosate comprise one or more, preferably one, mixing partner from groups (2) to (23).

Emphasis is given to active compound combinations according to the invention which, in addition to (1-2) glufosinate, comprised one or more, preferably one, mixing partner from groups (2) to (23).

Emphasis is given to active compound combinations according to the invention which, in addition to (1-3) glufosinate-ammonium, comprise one or more, preferably one, mixing partner from groups (2) to (23).

Preferred mixing partners of groups (2) to (23) are the active compounds below:

(2-1) azoxystrobin, (2-2) fluoxastrobin, (2-3) (2E)-2-{[6-(3-chloro-2-methylphenoxy)-5-fluoro-4-pyrimidinyl]oxy}phenyl)-2-(methoxyimino)-N-methylethanamide, (2-4) trifloxystrobin, (2-5) (2E)-2-(methoxyimino)-N-methyl-2-(2-{[({(1E)-1-[3-(trifluoromethyl)phenyl]ethylidene}amino)oxy]methyl}phenyl)ethanamide, (2-6) (2E)-2-(methoxyimino)-N-methyl-2-{2-[(E)-[({1-[3-(trifluoromethyl)phenyl]ethoxy}imino)methyl]phenyl}ethanamide, (2-8) 5-methoxy-2-methyl-4-(2-{[({(1E)-1-[3-(trifluoromethyl)-phenyl]ethylidene}amino)oxy]methyl}phenyl)-2,4-dihydro-3H-1,2,4-triazol-3-one, (2-11) picoxystrobin, (2-9) kresoxim-methyl, (2-10) dimoxystrobin, (2-12) pyraclostrobin, (2-13) metominostrobin, (3-3) propiconazole, (3-4) difenoconazole, (3-6) cyproconazole, (3-7) hexaconazole, (3-8) penconazole, (3-9) myclobutanil, (3-10) tetraconazole, (3-13) flusilazole, (3-15) prothioconazole, (3-16) fenbuconazole, (3-17) tebuconazole, (3-21) bitertanol, (3-22) triadimenol, (3-23) triadimefon, (3-12) epoxiconazole, (3-19) metconazole, (3-24) fluquinconazole, (4-1) dichlofluanid, (4-2) tolylfluanid, (5-1) iprovalicarb, (5-3) benthiavalicarb, (6-2) N-[2-(1,3-dimethylbutyl)phenyl]-5-fluoro-1,3-dimethyl-1H-pyrazole-4-carboxamide, (6-5) 3-(trifluoromethyl)-N-[2-(1,3-dimethylbutyl)phenyl]-5-fluoro-1-methyl-1H-pyrazole-4-carboxamide, (6-8) 5-fluoro-1,3-dimethyl-N-[2-(1,3,3-trimethylbutyl)phenyl]-1H-pyrazole-4-carboxamide, (6-13) N-[2-(1,3-dimethylbutyl)phenyl]-2-iodbenzamide, (6-15) N-[2-(1,3-dimethylbutyl)phenyl]-2-(trifluoromethyl)benzamide, (6-18) boscalid, (6-19) furametpyr, (6-21) penthiopyrad, (6-22) N-[2-(1,3-dimethylbutyl)phenyl]-1-methyl-4-(trifluoromethyl)-1H-pyrrole-3-carboxamide, (6-23) N-(3',4'-dichloro-5-fluoro-1,1'-biphenyl-2-yl)-3-(difluoromethyl)-1-methyl-1H-pyrazole-4-carboxamide, (6-24) 3-(difluoromethyl)-N-{3'-fluoro-4'-[(E)-(methoxyimino)methyl]-1,1'-biphenyl-2-yl}-1-methyl-1H-pyrazole-4-carboxamide, (6-25) 3-(trifluoromethyl)-N-{3'-fluoro-4'-[(E)-(methoxyimino)methyl]-1,1'-biphenyl-2-yl}-1-methyl-1H-pyrazole-4-carboxamide, (6-26) N-(3',4'-dichloro-1,1'-biphenyl-2-yl)-5-fluoro-1,3-dimethyl-1H-pyrazole-4-carboxamide, (6-29) N-(4'-bromo-1,1'-biphenyl-2-yl)-4-(difluoromethyl)-2-methyl-1,3-thiazole-5-carboxamide, (6-31) N-(4'-iodo-1,1'-biphenyl-2-yl)-4-(difluoromethyl)-2-methyl-1,3-thiazole-5-carboxamide, (6-32) N-(4'-chloro-3'-fluoro-1,1'-biphenyl-2-yl)-2-methyl-4-(difluoromethyl)-1,3-thiazole-5-carboxamide, (6-33) ethaboxam, (6-34) fenhexamid, (6-35) carpropamid, (6-36) 2-chloro-4-[(2-fluoro-2-methylpropanoyl)amino]-N,N-dimethylbenzamide, (6-37) cluopicolide, (6-38) zoxamide, (6-39) 3,4-dichloro-N-(2-cyanophenyl)isothiazole-5-carboxamide, (6-43) N-[2-(1,3-dimethylbutyl)phenyl]-1-methyl-4-(trifluoromethyl)-1H-pyrrole-3-carboxamide, (6-44) N-{2-[3-chloro-5-(trifluoromethyl)pyridin-2-yl]ethyl}-2-(trifluoromethyl)-benzamide, (6-45) N-(2-bicyclopropyl-2-yl-phenyl)-1-methyl-3-trifluoromethyl-1H-pyrazole-4-carboxamide, (6-46) N-(2-bicyclopropyl-2-yl-phenyl)-1-methyl-3-difluoromethyl-1H-pyrazole-4-carboxamide, (6-47) N-[2-(1'-methylbicylopropyl-2-yl)phenyl]-1-methyl-3-trifluoromethyl-1H-pyrazole-4-carboxamide, (6-48) N-[2-(1'-methylbicyclopropyl-2-yl)phenyl]-1-methyl-3-difluoromethyl-1H-pyrazole-4-carboxamide, (6-49) N-[1-(5-bromo-3-chloropyridin-2-yl)ethyl]-2,4-dichloronicotinamide, (6-50) N-(5-bromo-3-chloropyridin-2-yl)methyl-2,4-dichloronicotinamide, (6-51) N-(3',4'-dichloro-5-fluoro-1,1'-biphenyl-2-yl)-3-(difluoromethyl)-1-methyl-1H-pyrazole-4-carboxamide, (6-52) N-(3',4'-dichloro-5-fluoro-1,1'-biphenyl-2-yl)-3-(difluoromethyl)-1-methyl-1H-pyrazole-4-carboxamide, (6-53) 3-Difluoromethyl-1-methyl-1H-pyrazole-4-carboxylic acid [2-(3,3-dimethyl-butyl)-phenyl]-amide, (7-1) mancozeb, (7-2) maneb, (7-4) propineb, (7-5) thiram, (7-6) zineb, (8-1) benalaxyl, (8-2) furalaxyl, (8-3) metalaxyl, (8-4) metalaxyl-M, (8-5) benalaxyl-M, (9-1) cyprodinil, (9-2) mepanipyrim, (9-3) pyrimethanil, (10-1) 6-chloro-5-[(3,5-dimethylisoxazol-4-yl)sulphonyl]-2,2-difluoro-5H-[1,3]dioxolo[4,5-f]benzimidazole, (10-3) carbendazim, (11-1) diethofencarb, (11-2) propamocarb, (11-3) propamocarb hydrochloride, (11-4) propamocarb-fosetyl, (12-2) captan, (12-3) folpet, (12-4) iprodione, (12-5) procymidone, (13-1) dodine, (13-2) guazatine, (13-3) iminoctadine triacetate, (14-1) cyazofamid, (14-2) prochloraz, (14-3) triazoxide, (15-5) dimethomorph, (15-4) fenpropimorph, (16-2) fludioxonil, (17-1) fosetyl-Al, (17-2) phosphonic acid, (19-1) acibenzolar-S-methyl, (19-2) chlorothalonil, (19-3) cymoxanil, (19-5) famoxadone, (19-6) fluazinam, (19-9) oxadixyl, (19-10) spiroxamine, (19-7) copper oxychloride, (19-13) fenamidone, (19-22) 2-(4-chlorophenyl)-N-{2-[3-methoxy-4-(prop-2-yn-1-yloxy)phenyl]ethyl}-2-(prop-2-yn-1-yloxy)acetamide, (20-1) pencycuron, (20-2) thiophanate-methyl, (22-1) 5-chloro-N-[(1S)-2,2,2-trifluoro-1-methylethyl]-6-(2,4,6-trifluorophenyl)[1,2,4]triazolo-[1,5-a]pyrimidine-7-amine, (22-2) 5-chloro-N-[(1R)-1,2-dimethylpropyl]-6-(2,4,6-trifluorophenyl)-[1,2,4]triazolo[1,5-a]pyrimidine-7-amine, (22-4) 5-chloro-6-(2,4,6-trifluorophenyl)-7-(4-methylpiperidin-1-yl)[1,2,4]triazolo[1,5-a]pyrimidine, (23-1) 2-butoxy-6-iodo-3-propylbenzopyran-4-one, (23-2) 2-ethoxy-6-iodo-3-propylbenzopyran-4-one, (23-3) 6-iodo-2-propoxy-3-propylbenzopyran-4-one.

From among these compounds, the following are especially preferred for controlling rust diseases on soya bean plants:

(2-1) azoxystrobin, (2-2) fluoxastrobin, (2-4) trifloxystrobin, (2-6) (2E)-2-(methoxyimino)-N-methyl-2-{2-[(E)-({1-[3-(trifluoromethyl)phenyl]ethoxy}imino)methyl]phenyl}ethanamide, (2-8) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2-11) picoxystrobin, (2-9) kresoxim-methyl, (2-10) dimoxystrobin, (2-12) pyraclostrobin, (2-13) metominostrobin, (3-3) propiconazole, (3-4) difenoconazole, (3-6) cyproconazole, (3-7) hexaconazole, (3-8) penconazole, (3-9) myclobutanil, (3-10) tetraconazole, (3-13) flusilazole, (3-15) prothioconazole, (3-16) fenbuconazole, (3-17) tebuconazole, (3-21) bitertanol, (3-22) triadimenol, (3-23) triadimefon, (3-12) epoxiconazole, (3-19) metconazole, (3-24) fluquinconazole, (4-1) dichlofluanid, (4-2) tolylfluanid, (6-2) N-[2-(1,3-dimethylbutyl)phenyl]-5-fluoro-1,3-dimethyl-1H-pyrazole-4-carboxamide, (6-8) 5-fluoro-1,3-dimethyl-N-[2-(1,3,3-trimethylbutyl)phenyl]-1H-pyrazole-4-carboxamide, (6-13) N-[2-(1,3-dimethylbutyl)phenyl]-2-iodobenzamide, (6-15) N-[2-(1,3-dimethylbutyl)phenyl]-2-(trifluoromethyl)benzamide, (6-18) boscalid, (6-19) furametpyr, (6-21) penthiopyrad, (6-22) N-[2-(1,3-dimethylbutyl)phenyl]-1-methyl-4-(trifluoromethyl)-1H-pyrrole-3-carboxamide, (6-23) N-(3',4'-dichloro-5-fluoro-1,1'-biphenyl-2-yl)-3-(difluoromethyl)-1-methyl-1H-pyrazole-4-carboxamide, (6-26) N-(3',4'-dichloro-1,1'-biphenyl-2-yl)-5-fluoro-1,3-dimethyl-1H-pyrazole-4-carboxamide, (6-29) N-(4'-bromo-1,1'-biphenyl-2-yl)-4-(difluoromethyl)-2-methyl-1,3-thiazole-5-carboxamide, (6-31) N-(4'-iodo-1,1'-biphenyl-2-yl)-4-(difluoromethyl)-2-methyl-1,3-thiazole-5-carboxamide, (6-32) N-(4'-chloro-3'-fluoro-1,1'-biphenyl-2-yl)-2-methyl-4-(difluoromethyl)-1,3-thiazole-5-carboxamide, (6-39) 3,4-dichloro-N-(2-cyanophenyl)isothiazole-5-carboxamide, (6-43) N-[2-(1,3-dimethylbutyl)phenyl]-1-methyl-4-(trifluoromethyl)-1H-pyrrole-3-carboxamide, (6-45) N-(2-bicyclopropyl-2-yl-phenyl)-1-methyl-3-trifluoromethyl-1H-pyrazole-4-carboxamide, (6-46) N-(2-bicyclopropyl-2-yl-phenyl)-1-methyl-3-difluoromethyl-1H-pyrazole-4-carboxamide, (6-47) N-[2-(1'-methylbicyclopropyl-2-yl)phenyl]-1-methyl-3-trifluoromethyl-1H-pyrazole-4-carboxamide, (6-48) N-[2-(1'-methylbicyclopropyl-2-yl)phenyl]-1-methyl-3-difluoromethyl-1H-pyrazole-4-carboxamide, (6-49) N-[1-(5-bromo-3-chloropyridin-2-yl)ethyl]-2,4-dichloronicotinamide, (6-50) N-(5-bromo-3-chloropyridin-2-yl)methyl-2,4-dichloronicotinamide, (6-51) N-(3',4'-dichloro-5-fluoro-1,1'-biphenyl-2-yl)-3-(difluoromethyl)-1-methyl-1H-pyrazole-4-carboxamide, (6-52) N-(3',4'-dichloro-5-fluoro-1,1'-biphenyl-2-yl)-3-(difluoromethyl)-1-methyl-1H-pyrazole-4-carboxamide, (6-53) 3-Difluoromethyl-1-methyl-1H-pyrazole-4-carboxylic acid [2-(3,3-dimethyl-butyl)-phenyl]-amide, (7-1) mancozeb, (7-2) maneb, (7-4) propineb, (7-5) thiram, (7-6) zineb, (9-1) cyprodinil, (9-2) mepanipyrim, (9-3) pyrimethanil, (10-3) carbendazim, (11-1) diethofencarb, (12-2) captan, (12-3) folpet, (12-4) iprodione, (12-5) procymidone, (13-1) dodine, (13-2) guazatine, (13-3) iminoctadine triacetate, (14-2) prochloraz, (15-4) fenpropimorph, (16-2) fludioxonil, (19-1) acibenzolar-5-methyl, (19-2) chlorothalonil, (19-3) cymoxanil, (19-6) fluazinam, (19-10) spiroxamine, (19-7) copper oxychloride, (20-2) thiophanate-methyl, (22-1) 5-chloro-N-[(1S)-2,2,2-trifluoro-1-methylethyl]-6-(2,4,6-trifluorophenyl)-[1,2,4]triazolo[1,5-a]pyrimidine-7-amine, (22-2) 5-chloro-N-[(1R)-1,2-dimethylpropyl]-6-(2,4,6-trifluorophenyl)[1,2,4]triazolo[1,5-a]pyrimidine-7-amine, (22-4) 5-chloro-6-(2,4,6-trifluorophenyl)-7-(4-methylpiperidin-1-yl)[1,2,4]triazolo[1,5-a]pyrimidine.

Particularly preferred mixing partners of groups (2) to (23) are the following active compoounds:

(2-2) fluoxastrobin, (2-4) trifloxystrobin, (2-3) (2E)-2-(2-{[6-(3-chloro-2-methylphenoxy)-5-fluoro-4-pyrimidinyl]oxy}phenyl)-2-(methoxyimino)-N-methylethanamide, (3-15) prothioconazole, (3-17) tebuconazole, (3-21) bitertanol, (3-22) triadimenol, (3-24) fluquinconazole, (4-1) dichlofluanid, (4-2) tolylfluanid, (5-1) iprovalicarb, (6-2) N-[2-(1,3-dimethylbutyl)phenyl]-5-fluoro-1,3-dimethyl-1H-pyrazole-4-carboxamide, (6-8) 5-fluoro-1,3-dimethyl-N-[2-(1,3,3-trimethylbutyl)phenyl]-1H-pyrazole-4-carboxamide, (6-13) N-[2-(1,3-dimethylbutyl)phenyl]-2-iodobenzamide, (6-15) N-[2-(1,3-dimethylbutyl)-phenyl]-2-(trifluoromethyl)benzamide, (6-18) boscalid, (6-21) penthiopyrad, (6-22) N-[2-(1,3-dimethylbutyl)phenyl]-1-methyl-4-(trifluoromethyl)-1H-pyrrole-3-carboxamide, (6-23) N-(3',4'-dichloro-5-fluoro-1,1'-biphenyl-2-yl)-3-(difluoromethyl)-1-methyl-1H-pyrazole-4-carboxamide, (6-29) N-(4'-bromo-1,1'-biphenyl-2-yl)-4-(difluoromethyl)-2-methyl-1,3-thiazole-5-carboxamide, (6-31) N-(4'-iodo-1,1'-biphenyl-2-yl)-4-(difluoromethyl)-2-methyl-1,3-thiazole-5-carboxamide, (6-32) N-(4'-chloro-3'-fluoro-1,1'-biphenyl-2-yl)-2-methyl-4-(difluoromethyl)-1,3-thiazole-5-carboxamide, (6-34) fenhexamid, (6-35) carpropamid, (6-37) fluopicolide, (6-44) N-{2-[3-chloro-5-(trifluoromethyl)pyridin-2-yl]ethyl}-2-(trifluoromethyl)benzamide, (6-53) 3-Difluoromethyl-1-methyl-1H-pyrazole-4-carboxylic acid [2-(3,3-dimethylbutyl)-phenyl]-amide, (7-4) propineb, (8-4) metalaxyl-M, (8-5) benalaxyl-M, (9-3) pyrimethanil, (10-3) carbendazim, (11-4) propamocarb-fosetyl, (12-4) iprodione, (14-2) prochloraz, (14-3) triazoxide, (16-2) fludioxonil, (19-10) spiroxamine, (19-22) 2-(4-chlorophenyl)-N-{2-[3-methoxy-4-(prop-2-yn-1-yloxy)-phenyl]ethyl}-2-(prop-2-yn-1-yloxy)acetamide, (22-4) 5-chloro-6-(2,4,6-trifluorophenyl)-7-(4-methyl-piperidin-1-yl)[1,2,4]triazolo[1,5-a]pyrimidine.

From among these compounds, the following are especially preferred for controlling rust diseases on soya bean plants:

(2-2) fluoxastrobin, (2-4) trifloxystrobin, (3-15) prothioconazole, (3-17) tebuconazole, (3-21) bitertanol, (3-22) triadimenol, (3-24) fluquinconazole, (4-1) dichlofluanid, (4-2) tolylfluanid, (6-2) N-[2-(1,3-dimethylbutyl)phenyl]-5-fluoro-1,3-dimethyl-1H-pyrazole-4-carboxamide, (6-8)

5-fluoro-1,3-dimethyl-N-[2-(1,3,3-trimethylbutyl)phenyl]-1H-pyrazole-4-carboxamide, (6-13) N-[2-(1,3-dimethylbutyl)phenyl]-2-iodobenzamide, (6-15) N-[2-(1,3-dimethylbutyl)phenyl]-2-(trifluoromethyl)benzamide, (6-18) boscalid, (6-21) penthiopyrad, (6-22) N-[2-(1,3-dimethylbutyl)phenyl]-1-methyl-4-(trifluoromethyl)-1H-pyrrole-3-carboxamide, (6-23) N-(3',4'-dichloro-5-fluoro-1,1'-biphenyl-2-yl)-3-(difluoromethyl)-1-methyl-1H-pyrazole-4-carboxamide, (6-29) N-(4'-bromo-1,1'-biphenyl-2-yl)-4-(difluoromethyl)-2-methyl-1,3-thiazole-5-carboxamide, (6-31) N-(4'-iodo-1,1'-biphenyl-2-yl)-4-(difluoromethyl)-2-methyl-1,3-thiazole-5-carboxamide, (6-32) N-(4'-chloro-3'-fluoro-1,1'-biphenyl-2-yl)-2-methyl-4-(difluoromethyl)-1,3-thiazole-5-carboxamide, (6-53) 3-Difluoromethyl-1-methyl-1H-pyrazole-4-carboxylic acid [2-(3,3-dimethyl-butyl)-phenyl]-amide, (7-4) propineb, (9-3) pyrimethanil, (10-3) carbendazim, (12-4) iprodione, (14-2) prochloraz, (16-2) fludioxonil, (19-10) spiroxamine, (22-4) 5-chloro-6-(2,4,6-trifluorophenyl)-7-(4-methylpiperidin-1-yl)[1,2,4]triazolo[1,5-a]pyrimidine.

Preferred active compound combinations consisting of two groups of active compounds and comprising in each case at least one herbicide of groups (1) and at least one active compound of the stated groups (2) to (23) are described below.

Emphasis is given to the active compound combinations listed in Table 1 below:

TABLE 1

| No. | Herbicide | Active compound of groups (2) to (23) |
|---|---|---|
| 1 | (1-1) glyphosate | (2-2) fluoxastrobin |
| 2 | (1-1) glyphosate | (2-4) trifloxystrobin |
| 3 | (1-1) glyphosate | (2-3) (2E)-2-(2-{[6-(3-chloro-2-methylphenoxy)-5-fluoro-4-pyrimidinyl]oxy}phenyl)-2-(methoxyimino)-N-methylethanamide |
| 4 | (1-1) glyphosate | (3-15) pothioconazole |
| 5 | (1-1) glyphosate | (3-17) tebuconazole |
| 6 | (1-1) glyphosate | (3-21) bitertanol |
| 7 | (1-1) glyphosate | (3-22) triadimenol |
| 8 | (1-1) glyphosate | (3-24) fluquinconazole |
| 9 | (1-1) glyphosate | (4-1) dichlofluanid |
| 10 | (1-1) glyphosate | (4-2) tolylfluanid |
| 11 | (1-1) glyphosate | (5-1) iprovalicarb |
| 12 | (1-1) glyphosate | (6-2) N-[2-(1,3-dimethylbutyl)phenyl]-5-fluoro-1,3-dimethyl-1H-pyrazole-4-carboxamide |
| 13 | (1-1) glyphosate | (6-8) 5-fluoro-1,3-dimethyl-N-[2-(1,3,3-trimethylbutyl)phenyl]-1H-pyrazole-4-carboxamide |
| 14 | (1-1) glyphosate | (6-13) N-[2-(1,3-dimethylbutyl)phenyl]-2-iodobenzamide |
| 15 | (1-1) glyphosate | (6-15) N-[2-(1,3-dimethylbutyl)phenyl]-2-(trifluoromethyl)benzamide |
| 16 | (1-1) glyphosate | (6-18) boscalid |
| 17 | (1-1) glyphosate | (6-21) penthiopyrad |
| 18 | (1-1) glyphosate | (6-22) N-[2-(1,3-dimethylbutyl)phenyl]-1-methyl-4-(trifluoromethyl)-1H-pyrrole-3-carboxamide |
| 19 | (1-1) glyphosate | (6-23) N-(3',4'-dichloro-5-fluoro-1,1'-biphenyl-2-yl)-3-(difluoromethyl)-1-methyl-1H-pyrazole-4-carboxamide |
| 20 | (1-1) glyphosate | (6-29) N-(4'-bromo-1,1'-biphenyl-2-yl)-4-(difluoromethyl)-2-methyl-1,3-thiazole-5-carboxamide |
| 21 | (1-1) glyphosate | (6-31) N-(4'-iodo-1,1'-biphenyl-2-yl)-4-(difluoromethyl)-2-methyl-1,3-thiazole-5-carboxamide |
| 22 | (1-1) glyphosate | (6-32) N-(4'-chloro-3'-fluoro-1,1'-biphenyl-2-yl)-2-methyl-4-(difluoromethyl)-1,3-thiazole-5-carboxamide |
| 23 | (1-1) glyphosate | (6-34) fenhexamid |
| 24 | (1-1) glyphosate | (6-35) carpropamid |
| 25 | (1-1) glyphosate | (6-37) fluopicolide |
| 26 | (1-1) glyphosate | (6-44) N-{2-[3-chloro-5-(trifluoromethyl)pyridin-2-yl]ethyl}-2-(trifluoromethyl)benzamide |
| 27 | (1-1) glyphosate | (6-53) 3-Difluoromethyl-1-methyl-1H-pyrazole-4-carboxylic acid [2-(3,3-dimethyl-butyl)-phenyl]-amide |
| 28 | (1-1) glyphosate | (7-4) propineb |
| 29 | (1-1) glyphosate | (8-4) metalaxyl-M |
| 30 | (1-1) glyphosate | (8-5) benalaxyl-M |
| 31 | (1-1) glyphosate | (9-3) pyrimethanil |
| 32 | (1-1) glyphosate | (10-3) carbendazim |
| 33 | (1-1) glyphosate | (11-4) propamocarb-fosetyl |
| 34 | (1-1) glyphosate | (12-4) iprodione |
| 35 | (1-1) glyphosate | (14-2) prochloraz |
| 36 | (1-1) glyphosate | (14-3) triazoxide |
| 37 | (1-1) glyphosate | (16-2) fludioxonil |
| 38 | (1-1) glyphosate | (19-10) spiroxamine |
| 39 | (1-1) glyphosate | (19-22) 2-(4-chlorophenyl)-N-{2-[3-methoxy-4-(prop-2-yn-1-yloxy)phenyl]ethyl}-2-(prop-2-yn-1-yloxy)acetamide |
| 40 | (1-1) glyphosate | (22-4) 5-chloro-6-(2,4,6-trifluorophenyl)-7-(4-methylpiperidin-1-yl)[1,2,4]triazolo[1,5-a]pyrimidine |
| 41 | (1-2) glufosinate | (2-2) fluoxastrobin |
| 42 | (1-2) glufosinate | (2-4) trifloxystrobin |
| 43 | (1-2) glufosinate | (2-3) (2E)-2-(2-{[6-(3-chloro-2-methylphenoxy)-5-fluoro-4-pyrimidinyl]oxy}phenyl)-2-(methoxyimino)-N-methylethanamide |
| 44 | (1-2) glufosinate | (3-15) prothioconazole |
| 45 | (1-2) glufosinate | (3-17) tebuconazole |
| 46 | (1-2) glufosinate | (3-21) bitertanol |

TABLE 1-continued

| No. | Herbicide | Active compound of groups (2) to (23) |
|---|---|---|
| 47 | (1-2) glufosinate | (3-22) triadimenol |
| 48 | (1-2) glufosinate | (3-24) fluquinconazole |
| 49 | (1-2) glufosinate | (4-1) dichlofluanid |
| 50 | (1-2) glufosinate | (4-2) tolylfluanid |
| 51 | (1-2) glufosinate | (5-1) iprovalicarb |
| 52 | (1-2) glufosinate | (6-2) N-[2-(1,3-dimethylbutyl)phenyl]-5-fluoro-1,3-dimethyl-1H-pyrazole-4-carboxamide |
| 53 | (1-2) glufosinate | (6-8) 5-fluoro-1,3-dimethyl-N-[2-(1,3,3-trimethylbutyl)phenyl]-1H-pyrazole-4-carboxamide |
| 54 | (1-2) glufosinate | (6-13) N-[2-(1,3-dimethylbutyl)phenyl]-2-iodobenzamide |
| 55 | (1-2) glufosinate | (6-15) N-[2-(1,3-dimethylbutyl)phenyl]-2-(trifluoromethyl)benzamide |
| 56 | (1-2) glufosinate | (6-18) boscalid |
| 57 | (1-2) glufosinate | (6-21) penthiopyrad |
| 58 | (1-2) glufosinate | (6-22) N-[2-(1,3-dimethylbutyl)phenyl]-1-methyl-4-(trifluoromethyl)-1H-pyrrole-3-carboxamide |
| 59 | (1-2) glufosinate | (6-23) N-(3',4'-dichloro-5-fluoro-1,1'-biphenyl-2-yl)-3-(difluoromethyl)-1-methyl-1H-pyrazole-4-carboxamide |
| 60 | (1-2) glufosinate | (6-29) N-(4'-bromo-1,1'-biphenyl-2-yl)-4-(difluoromethyl)-2-methyl-1,3-thiazole-5-carboxamide |
| 61 | (1-2) glufosinate | (6-31) N-(4'-iodo-1,1'-biphenyl-2-yl)-4-(difluoromethyl)-2-methyl-1,3-thiazole-5-carboxamide |
| 62 | (1-2) glufosinate | (6-32) N-(4'-chloro-3'-fluoro-1,1'-biphenyl-2-yl)-2-methyl-4-(difluoromethyl)-1,3-thiazole-5-carboxamide |
| 63 | (1-2) glufosinate | (6-34) fenhexamid |
| 64 | (1-2) glufosinate | (6-35) carpropamid |
| 65 | (1-2) glufosinate | (6-37) fluopicolide |
| 66 | (1-2) glufosinate | (6-44) N-{2-[3-chloro-5-(trifluoromethyl)pyridin-2-yl]ethyl}-2-(trifluoromethyl)benzamide |
| 67 | (1-2) glufosinate | (6-53) 3-Difluoromethyl-1-methyl-1H-pyrazole-4-carboxylic acid [2-(3,3-dimethyl-butyl)-phenyl]-amide |
| 68 | (1-2) glufosinate | (7-4) propineb |
| 69 | (1-2) glufosinate | (8-4) metalaxyl-M |
| 70 | (1-2) glufosinate | (8-5) benalaxyl-M |
| 71 | (1-2) glufosinate | (9-3) pyrimethanil |
| 72 | (1-2) glufosinate | (10-3) carbendazim |
| 73 | (1-2) glufosinate | (11-4) propamocarb-fosetyl |
| 74 | (1-2) glufosinate | (12-4) iprodione |
| 75 | (1-2) glufosinate | (14-2) prochloraz |
| 76 | (1-2) glufosinate | (14-3) triazoxide |
| 77 | (1-2) glufosinate | (16-2) fludioxonil |
| 78 | (1-2) glufosinate | (19-10) spiroxamine |
| 79 | (1-2) glufosinate | (19-22) 2-(4-chlorophenyl)-N-{2-[3-methoxy-4-(prop-2-yn-1-yloxy)phenyl]ethyl}-2-(prop-2-yn-1-yloxy)acetamide |
| 80 | (1-2) glufosinate | (22-4) 5-chloro-6-(2,4,6-trifluorophenyl)-7-(4-methylpiperidin-1-yl)[1,2,4]triazolo[1,5-a]pyrimidine |
| 81 | (1-3) glufosinate-ammonium | (2-2) fluoxastrobin |
| 82 | (1-3) glufosinate-ammonium | (2-4) trifloxystrobin |
| 83 | (1-3) glufosinate-ammonium | (2-3) (2E)-2-(2-{[6-(3-chloro-2-methylphenoxy)-5-fluoro-4-pyrimidinyl]oxy}phenyl)-2-(methoxyimino)-N-methylethanamide |
| 84 | (1-3) glufosinate-ammonium | (3-15) prothioconazole |
| 85 | (1-3) glufosinate-ammonium | (3-17) tebuconazole |
| 86 | (1-3) glufosinate-ammonium | (3-21) bitertanol |
| 87 | (1-3) glufosinate-ammonium | (3-22) triadimenol |
| 88 | (1-3) glufosinate-ammonium | (3-24) fluquinconazole |
| 89 | (1-3) glufosinate-ammonium | (4-1) dichlofluanid |
| 90 | (1-3) glufosinate-ammonium | (4-2) tolylfluanid |
| 91 | (1-3) glufosinate-ammonium | (5-1) iprovalicarb |
| 92 | (1-3) glufosinate-ammonium | (6-2) N-[2-(1,3-dimethylbutyl)phenyl]-5-fluoro-1,3-dimethyl-1H-pyrazole-4-carboxamide |
| 93 | (1-3) glufosinate-ammonium | (6-8) 5-fluoro-1,3-dimethyl-N-[2-(1,3,3-trimethylbutyl)phenyl]-1H-pyrazole-4-carboxamide |
| 94 | (1-3) glufosinate-ammonium | (6-13) N-[2-(1,3-dimethylbutyl)phenyl]-2-iodobenzamide |
| 95 | (1-3) glufosinate-ammonium | (6-15) N-[2-(1,3-dimethylbutyl)phenyl]-2-(trifluoro-methyl)benzamide |
| 96 | (1-3) glufosinate-ammonium | (6-18) boscalid |
| 97 | (1-3) glufosinate-ammonium | (6-21) penthiopyrad |
| 98 | (1-3) glufosinate-ammonium | (6-22) N-[2-(1,3-dimethylbutyl)phenyl]-1-methyl-4-(trifluoromethyl)-1H-pyrrole-3-carboxamide |
| 99 | (1-3) glufosinate-ammonium | (6-23) N-(3',4'-dichloro-5-fluoro-1,1'-biphenyl-2-yl)-3-(difluoromethyl)-1-methyl-1H-pyrazole-4-carboxamide |
| 100 | (1-3) glufosinate-ammonium | (6-29) N-(4'-bromo-1,1'-biphenyl-2-yl)-4-(difluoromethyl)-2-methyl-1,3-thiazole-5-carboxamide |
| 101 | (1-3) glufosinate-ammonium | (6-31) N-(4'-iodo-1,1'-biphenyl-2-yl)-4-(difluoromethyl)-2-methyl-1,3-thiazole-5-carboxamide |
| 102 | (1-3) glufosinate-ammonium | (6-32) N-(4'-chloro-3'-fluoro-1,1'-biphenyl-2-yl)-2-methyl-4-(difluoromethyl)-1,3-thiazole-5-carboxamide |
| 103 | (1-3) glufosinate-ammonium | (6-34) fenhexamid |

TABLE 1-continued

| No. | Herbicide | Active compound of groups (2) to (23) |
|---|---|---|
| 104 | (1-3) glufosinate-ammonium | (6-35) carpropamid |
| 105 | (1-3) glufosinate-ammonium | (6-37) fluopicolide |
| 106 | (1-3) glufosinate-ammonium | (6-44) N-{2-[3-chloro-5-(trifluoromethyl)pyridin-2-yl]ethyl}-2-(trifluoromethyl)benzamide |
| 107 | (1-3) glufosinate-ammonium | (6-53) 3-Difluoromethyl-1-methyl-1H-pyrazole-4-carboxylic acid [2-(3,3-dimethyl-butyl)-phenyl]-amide |
| 108 | (1-3) glufosinate-ammonium | (7-4) propineb |
| 109 | (1-3) glufosinate-ammonium | (8-4) metalaxyl-M |
| 110 | (1-3) glufosinate-ammonium | (8-5) menalaxyl-M |
| 111 | (1-3) glufosinate-ammonium | (9-3) pyrimethanil |
| 112 | (1-3) glufosinate-ammonium | (10-3) carbendazim |
| 113 | (1-3) glufosinate-ammonium | (11-4) propamocarb-fosetyl |
| 114 | (1-3) glufosinate-ammonium | (12-4) iprodione |
| 115 | (1-3) glufosinate-ammonium | (14-2) prochloraz |
| 116 | (1-3) glufosinate-ammonium | (14-3) triazoxide |
| 117 | (1-3) glufosinate-ammonium | (16-2) fludioxonil |
| 118 | (1-3) glufosinate-ammonium | (19-10) spiroxamine |
| 119 | (1-3) glufosinate-ammonium | (19-22) 2-(4-chlorophenyl)-N-{2-[3-methoxy-4-(prop-2-yn-1-yloxy)phenyl]ethyl}-2-(prop-2-yn-1-yloxy)acetamide |
| 120 | (1-3) glufosinate-ammonium | (22-4) 5-chloro-6-(2,4,6-trifluorophenyl)-7-(4-methylpiperidin-1-yl)[1,2,4]triazolo[1,5-a]pyrimidine |

From among these mixtures, the mixtures having the following numbers are especially preferred for controlling rust diseases on soya bean plants: 1-2, 4-10, 12-22, 28, 31-32, 34-35, 37-38, 40-42, 44-50, 52-62, 68, 71-72, 74-75, 77-78, 80-82, 84-90, 92-102, 108, 111-112, 114-115, 117-118 and 120.

In addition to one active compound of group (1), the active compound combinations according to the invention comprise at least one active compound from the compounds of groups (2) to (23). In addition, they may also comprise further fungicidally active components.

Thus, for example, each of the active compound combinations listed in Table 1 may comprise a third active compound selected from the list below:

(2-1) azoxystrobin, (2-2) fluoxastrobin, (2-3) (2E)-2-(2-{[6-(3-chloro-2-methylphenoxy)-5-fluoro-4-pyrimidinyl]oxy}phenyl)-2-(methoxyimino)-N-methylethanamide, (2-4) trifloxystrobin, (2-5) (2E)-2-(methoxyimino)-N-methyl-2-(2-{[({(1E)-1-[3-(trifluoromethyl)phenyl]ethylidene}amino)oxy]methyl}phenyl)ethanamide, (2-6) (2E)-2-(methoxyimino)-N-methyl-2-{2-[(E)-({1-[3-(trifluoromethyl)phenyl]ethoxy}imino)methyl]phenyl}ethanamide, (2-7) orysastrobin, (2-8) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2-9) kresoxim-methyl, (2-10) dimoxystrobin, (2-11) picoxystrobin, (2-12) pyraclostrobin, (2-13) metominostrobin, (2-14) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (2-15) enestroburin, (3-1) azaconazole, (3-2) etaconazole, (3-3) propiconazole, (3-4) difenoconazole, (3-5) bromuconazole, (3-6) cyproconazole, (3-7) hexaconazole, (3-8) penconazole, (3-9) myclobutanil, (3-10) tetraconazole, (3-11) flutriafol, (3-12) epoxiconazole, (3-13) flusilazole, (3-14) simeconazole, (3-15) prothioconazole, (3-16) fenbuconazole, (3-17) tebuconazole, (3-18) ipconazole, (3-19) metconazole, (3-20) triticonazole, (3-21) bitertanol, (3-22) triadimenol, (3-23) triadimefon, (3-24) fluquinconazole, (3-25) quinconazole, (3-26) amisulbrom, (4-1) dichlofluanid, (4-2) tolylfluanid, (4-3) N-(4-chloro-2-nitrophenyl)N-ethyl-4-methylbenzene sulphonamide, (5-1) iprovalicarb, (5-2) $N^1$-[2-(4-{[3-(4-chlorophenyl)-2-propynyl]oxy}-3-methoxyphenyl)-ethyl]-$N^2$-(methylsulphonyl)-D-valinamide, (5-3) benthiavalicarb, (6-1) N-[2-(1,3-dimethylbutyl)-phenyl]-1,3-dimethyl-1H-pyrazole-4-carboxamide, (6-2) N-[2-(1,3-dimethylbutyl)phenyl]-5-fluoro-1,3-dimethyl-1H-pyrazole-4-carboxamide, (6-3) N-[2-(1,3-dimethylbutyl)phenyl]-5-chloro-1,3-dimethyl-1H-pyrazole-4-carboxamide, (6-4) 3-(difluoromethyl)-N-[2-(1,3-dimethylbutyl)phenyl]-1-methyl-1H-pyrazole-4-carboxamide, (6-5) 3-(trifluoromethyl)-N-[2-(1,3-dimethylbutyl)phenyl]-5-fluoro-1-methyl-1H-pyrazole-4-carboxamide, (6-6) 3-(trifluoromethyl)-N-[2-(1,3-dimethylbutyl)phenyl]-5-chloro-1-methyl-1H-pyrazole-4-carboxamide, (6-7) 1,3-dimethyl-N-[2-(1,3,3-trimethylbutyl)phenyl]-1H-pyrazole-4-carboxamide, (6-8) 5-fluoro-1,3-dimethyl-N-[2-(1,3,3-trimethylbutyl)phenyl]-1H-pyrazole-4-carboxamide, (6-9) 3-(difluoromethyl)-1-methyl-N-[2-(1,3,3-trimethylbutyl)phenyl]-1H-pyrazole-4-carboxamide, (6-10) 3-(trifluoromethyl)-1-methyl-N-[2-(1,3,3-trimethylbutyl)phenyl]-1H-pyrazole-4-carboxamide, (6-11) 3-(trifluoromethyl)-5-fluoro-1-methyl-N-[2-(1,3,3-trimethylbutyl)phenyl]-1H-pyrazole-4-carboxamide, (6-12) 3-(trifluoromethyl)-5-chloro-1-methyl-N-[2-(1,3,3-trimethylbutyl)phenyl]-1H-pyrazole-4-carboxamide, (6-13) N-[2-(1,3-dimethylbutyl)phenyl]-2-iodobenzamide, (6-14) 2-iodo-N-[2-(1,3,3-trimethylbutyl)phenyl]benzamide, (6-15) N-[2-(1,3-dimethylbutyl)phenyl]-2-(trifluoromethyl)benzamide, (6-16) 2-(trifluoromethyl)-N-[2-(1,3,3-trimethylbutyl)phenyl]benzamide, (6-17) 2-chloro-N-(1,1,3-trimethylindan-4-yl)nicotinamide, (6-18) boscalid, (6-19) furametpyr, (6-20) N-3-p-tolythiophen-2-yl)-1-methyl-3-trifluoromethyl-1H-pyrazole-4-carboxamide, (6-21) penthiopyrad, (6-22) N-[2-(1,3-dimethylbutyl)phenyl]-1-methyl-4-(trifluoromethyl)-1H-pyrrole-3-carboxamide, (6-23) N-(3',4'-dichloro-5-fluoro-1,1'-biphenyl-2-yl)-3-(difluoromethyl)-1-methyl-1H-pyrazole-4-carboxamide, (6-24) 3-(difluoromethyl)-N-{3'-fluoro-4'-[(E)-(methoxyimino)methyl]-1,1'-biphenyl-2-yl}-1-methyl-1H-pyrazole-4-carboxamide, (6-25) 3-(trifluoromethyl)-N-{3'-fluoro-4'-[(E)-(methoxyimino)methyl]-1,1'-biphenyl-2-yl}-1-methyl-1H-pyrazole-4-carboxamide, (6-26) N-(3',4'-dichloro-1,1'-biphenyl-2-yl)-5-fluoro-1,3-dimethyl-1H-pyrazole-4-carboxamide, (6-27) N-(4'-chloro-3'-fluoro-1,1'-biphenyl-2-yl)-2-methyl-4-(trifluoromethyl)-1,3-thiazole-5-carboxamide, (6-28) N-(4'-chloro-1,1'-biphenyl-2-yl)-4-(difluoromethyl)-2-methyl-1,3-thiazole-5-carboxamide, (6-29) N-(4'-bromo-1,1'-biphenyl-2-yl)-4-(difluoromethyl)-2-methyl-1,3-thiazole-5- carboxamide, (6-30) 4-(difluoromethyl)-2-methyl-N-[4'-(trifluoromethyl)-1,1'-biphenyl-2-yl]-1,3-thiazole-5-carboxamide, (6-31) N-(4'-iodo-1,1'-biphenyl-2-yl)-4-(difluoromethyl)-2-methyl-1,3-thiazole-5-carboxamide, (6-32) N-(4'-chloro-3'-fluoro-1,1'-biphenyl-2-yl)-2-methyl-4-(difluoromethyl)-1,3-thiazole-5-carboxamide, (6-33) ethaboxam, (6-34) fenhexamid, (6-35) carpropamid, (6-36) 2-chloro-4-(2-fluoro-2-methylpropionylamino)-N,N-dimethylbenzamide, (6-37) fluopicolide, (6-38) zoxamide, (6-39) 3,4-dichloro-N-(2-cyanophenyl)isothiazole-5-carboxamide, (6-40) carboxin, (6-41) tiadinil, (6-42) silthiofam, (6-43) N-[2-(1,3-dimethylbutyl)phenyl]-1-methyl-4-(trifluoromethyl)-1H-pyrrole-3-carboxamide, (6-44) N-{2-[3-chloro-5-(trifluoromethyl)pyridin-2-yl]ethyl}-2-(trifluoromethyl) benzamide, (6-45) N-(2-bicyclopropyl-2-yl-phenyl)-1-methyl-3-trifluoromethyl-1H-pyrazole-4-carboxamide, (6-46) N-(2-bicyclopropyl-2-yl-phenyl)-1-methyl-3-difluoromethyl-1H-pyrazole-4-carboxamide, (6-47) N-[2-(1'-methylbicyclopropyl-2-yl)phenyl]-1-methyl-3-trifluoromethyl-1H-pyrazole-4-carboxamide, (6-48) N-[2-(1'-methylbicyclopropyl-2-yl)phenyl]-1-methyl-3-difluoromethyl-1H-pyrazole-4-carboxamide, (6-49) N-[1-(5-bromo-3-chloropyridin-2-yl)ethyl]-2,4-dichloronicotinamide, (6-50) N-(5-bromo-3-chloropyridin-2-yl)methyl-2,4-dichloronicotinamide, (6-51) N-(3',4'-dichloro-5-fluoro-1,1'-biphenyl-2-yl)-3-(difluoromethyl)-1-methyl-1H-pyrazole-4-carboxamide, (6-52) N-(3',4'-dichloro-5-fluoro-1,1'-biphenyl-2-yl)-3-(difluoromethyl)-1-methyl-1H-pyrazole-4-carboxamide, (6-53) 3-difluoromethyl-1-methyl-1H-pyrazole-4-carboxylic acid [2-(3,3-dimethyl-butyl)-phenyl]-amide, (7-1) mancozeb, (7-2) maneb, (7-3) metiram, (7-4) propineb, (7-5) thiram, (7-6) zineb, (7-7) ziram, (8-1) benalaxyl, (8-2) furalaxyl, (8-3) metalaxyl, (8-4) metalaxyl-m, (8-5) benalaxyl-m, (9-1) cyprodinil, (9-2) mepanipyrim, (9-3) pyrimethanil, (10-1) 6-chloro-5-[(3,5-dimethylisoxazol-4-yl)sulphonyl]-2,2-difluoro-5H-[1,3]-dioxolo[4,5-f]benzimidazole, (10-2) benomyl, (10-3) carbendazim, (10-4) chlorofenazole, (10-5) fuberidazole, (10-6) thiabendazole, (11-1) diethofencarb, (11-2) propamocarb, (11-3) propamocarb hydrochloride, (11-4) propamocarb-fosetyl, (12-1) captafol, (12-2) captan, (12-3) folpet, (12-4) iprodione, (12-5) procymidone, (12-6) vinclozolin, (13-1) dodine, (13-2) guazatine, (13-3) iminoctadine triacetate, (13-4) iminoctadine tris(albesilate), (14-1) cyazofamid, (14-2) prochloraz, (14-3) triazoxide, (14-4) pefurazoate, (15-1) aldimorph, (15-2) tridemorph, (15-3) dodemorph, (15-4) fenpropimorph, (15-5) dimethomorph, (15-6) flumorph, (16-1) fenpiclonil, (16-2) fludioxonil, (16-3) pyrrolnitrin, (17-1) fosetyl-Al, (17-2) phosphonic acid, (18-1) 2-(2,3-dihydro-1H-inden-5-yl)-N-[2-(3,4-dimethoxyphenyl)-ethyl]-2-(methoxyimino)acetamide, (18-2) N-[2-(3,4-dimethoxyphenyl)ethyl]-2-(methoxyimino)-2-(5,6,7,8-tetrahydronaphthalen-2-yl)acetamide, (18-3) 2-(4-chlorophenyl)-N-[2-(3,4-dimethoxyphenyl)-ethyl]-2-(methoxyimino)acetamide, (18-4) 2-(4-bromophenyl)-N-[2-(3,4-dimethoxyphenyl)ethyl]-2-(methoxyimino)acetamide, (18-5) 2-(4-methylphenyl)-N-[2-(3,4-dimethoxyphenyl)ethyl]-2-(methoxyimino)acetamide, (18-6) 2-(4-ethylphenyl)-N-[2-(3,4-dimethoxyphenyl)ethyl]-2-(methoxyimino)acetamide, (19-1) acibenzolar-S-methyl, (19-2) chlorothalonil, (19-3) cymoxanil, (19-4) edifenphos, (19-5) famoxadone, (19-6) fluazinam, (19-7) copper oxychloride, (19-8) copper hydroxide, (19-9) oxadixyl, (19-10) spiroxamine, (19-11) dithianon, (19-12) metrafenone, (19-13) fenamidone, (19-14) 2,3-dibutyl-6-chlorothieno[2,3-d]pyrimidine-4(3H)-one, (19-15) probenazole, (19-16) isoprothiolane, (19-17) kasugamycin, (19-18) phthalide, (19-19) ferimzone, (19-20) tricyclazole, (19-21) N-({4-[(cyclopropylamino)carbonyl]phenyl}sulphonyl)-2-methoxybenzamide, (19-22) 2-(4-chlorophenyl)-N-{2-[3-methoxy-4-(prop-2-yn-1-yloxy)phenyl]ethyl}-2-(prop-2-yn-1-yloxy)acetamide, (19-23) proquinazid, (19-24) quinoxyfen, (19-25) cyflufenamid, (19-26) pyribencarb, (19-27) 3-[5-(4-chlorophenyl)-2,3-dimethyl-3-isoxazolidinyl]pyridine, (20-1) pencycuron, (20-2) thiophanate-methyl, (20-3) thiophanate-ethyl, (21-1) fenoxanil, (21-2) diclocymet, (22-1) 5-chloro-N-[(1S)-2,2,2-trifluoro-1-methylethyl]-6-(2,4,6-trifluorophenyl)[1,2,4]triazolo[1,5-a]pyrimidine-7-amine, (22-2) 5-chloro-N-[(1R)-1,2-dimethylpropyl]-6-(2,4,6-trifluorophenyl)[1,2,4]triazolo[1,5-a]pyrimidine-7-amine, (22-3) 5-chloro-6-(2-chloro-6-fluorophenyl)-7-(4-methylpiperidin-1-yl)[1,2,4]triazolo[1,5-a]pyrimidine, (22-4) 5-chloro-6-(2,4,6-trifluorophenyl)-7-(4-methylpiperidin-1-yl)[1,2,4]triazolo[1,5-a]pyrimidine, (23-1) 2-butoxy-6-iodo-3-propylbenzopyran-4-one, (23-2) 2-ethoxy-6-iodo-3-propylbenzopyran-4-one, (23-3) 6-iodo-2-propoxy-3-propylbenzopyran-4-one, (23-4) 2-but-2-ynyloxy-6-iodo-3-propylbenzopyran-4-one, (23-5) 6-iodo-2-(1-methylbutoxy)-3-propylbenzopyran-4-one, (23-6) 2-but-3-enyloxy-6-iodobenzopyran-4-one, (23-7) 3-butyl-6-iodo-2-isopropoxybenzopyran-4-one.

The synergistic effect is particularly pronounced when the active compounds in the active compound combinations according to the invention are present in certain weight ratios. However, the weight ratios of the active compounds in the active compound combinations can be varied within a relatively wide range. In general, the combinations according to the invention comprise active compounds of group (1) and a mixing partner from one of groups (2) to (23) in the mixing ratios given in an exemplary manner in Table 2 below.

The mixing ratios are based on weight ratios. The ratio is to be understood as meaning active compound of group (1): mixing partner.

TABLE 2

Mixing ratios

| | Mixing partner | Preferred mixing ratio | Particularly preferred mixing ratio |
|---|---|---|---|
| Group (2): | strobilurins | 1:100 to 1:0.01 | 1:5 to 1:0.01 |
| Group (3): | triazoles | 1:100 to 1:0.01 | 1:5 to 1:0.01 |
| Group (4): | sulphenamides/sulphonamides | 1:100 to 1:0.01 | 1:10 to 1:0.1 |
| Group (5): | valinamides | 1:100 to 1:0.01 | 1:5 to 1:0.01 |
| Group (6): | carboxamides | 1:100 to 1:0.01 | 1:5 to 1:0.01 |
| Group (7): | dithiocarbamates | 1:100 to 1:0.01 | 1:25 to 1:0.2 |
| Group (8): | acylalanines | 1:100 to 1:0.01 | 1:12 to 1:0.02 |
| Group (9): | anilinopyrimidines | 1:100 to 1:0.01 | 1:10 to 1:0.05 |
| Group (10): | benzimidazoles | 1:100 to 1:0.01 | 1:5 to 1:0.01 |
| Group (11): | carbamates excluding (11-1) | 1:100 to 1:0.01 | 1:100 to 1:0.2 |

TABLE 2-continued

Mixing ratios

| | Mixing partner | Preferred mixing ratio | Particularly preferred mixing ratio |
|---|---|---|---|
| (11-1): | diethofencarb | 1:100 to 1:0.01 | 1:5 to 1:0.01 |
| Group (12): | (12-1)/(12-2)/(12-3) | 1:100 to 1:0.01 | 1:25 to 1:0.2 |
| Group (12): | (12-4)/(12-5)/(12-6) | 1:100 to 1:0.01 | 1:10 to 1:0.05 |
| Group (13): | guanidines | 1:100 to 1:0.01 | 1:10 to 1:0.01 |
| Group (14): | imidazoles | 1:100 to 1:0.01 | 1:5 to 1:0.01 |
| Group (15): | morpholines | 1:100 to 1:0.01 | 1:5 to 1:0.01 |
| Group (16): | pyrroles | 1:100 to 1:0.01 | 1:5 to 1:0.01 |
| Group (17): | phosphonates | 1:100 to 1:0.01 | 1:25 to 1:0.2 |
| Group (18): | phenylethanamides | 1:100 to 1:0.01 | 1:5 to 1:0.01 |
| (19-1): | acibenzolar-s-methyl | 1:100 to 1:0.01 | 1:5 to 1:0.01 |
| (19-2): | chlorothalonil | 1:100 to 1:0.01 | 1:25 to 1:0.2 |
| (19-3): | cymoxanil | 1:100 to 1:0.01 | 1:5 to 1:0.01 |
| (19-4): | edifenphos | 1:100 to 1:0.01 | 1:5 to 1:0.01 |
| (19-5): | famoxadone | 1:100 to 1:0.01 | 1:5 to 1:0.01 |
| (19-6): | fluazinam | 1:100 to 1:0.01 | 1:5 to 1:0.01 |
| (19-7): | copper oxychloride | 1:100 to 1:0.01 | 1:100 to 1:0.2 |
| (19-8): | copper hydroxide | 1:100 to 1:0.01 | 1:100 to 1:0.2 |
| (19-9): | oxadixyl | 1:100 to 1:0.01 | 1:12 to 1:0.02 |
| (19-10): | spiroxamine | 1:100 to 1:0.01 | 1:5 to 1:0.01 |
| (19-11) | dithianon | 1:100 to 1:0.01 | 1:5 to 1:0.01 |
| (19-12) | metrafenone | 1:100 to 1:0.01 | 1:5 to 1:0.01 |
| (19-13) | fenamidone | 1:100 to 1:0.01 | 1:5 to 1:0.01 |
| (19-14): | 2,3-dibutyl-6-chlorothieno[2,3-d]-pyrimidin-4(3H)-one | 1:100 to 1:0.01 | 1:5 to 1:0.01 |
| (19-15): | probenazole | 1:100 to 1:0.01 | 1:100 to 1:0.2 |
| (19-16): | isoprothiolane | 1:100 to 1:0.01 | 1:100 to 1:0.2 |
| (19-17): | kasugamycin | 1:100 to 1:0.01 | 1:5 to 1:0.01 |
| (19-18): | phthalide | 1:100 to 1:0.01 | 1:100 to 1:0.2 |
| (19-19): | ferimzone | 1:100 to 1:0.01 | 1:5 to 1:0.01 |
| (19-20): | tricyclazole | 1:100 to 1:0.01 | 1:5 to 1:0.01 |
| (19-21): | N-({4-[(cyclopropylamino)-carbonyl]phenyl}sulphonyl)-2-methoxybenzamide | 1:100 to 1:0.01 | 1:100 to 1:0.2 |
| (19-22): | 2-(4-chlorophenyl)-N-{2-[3-methoxy-4-(prop-2-yn-1-yloxy)phenyl]ethyl}-2-(prop-2-yn-1-yloxy)acetamide | 1:100 to 1:0.01 | 1:5 to 1:0.01 |
| (19-23): | proquinazid | 1:100 to 1:0.01 | 1:5 to 1:0.01 |
| (19-24): | quinoxyfen | 1:100 to 1:0.01 | 1:5 to 1:0.01 |
| (19-25) | cyflufenamid | 1:100 to 1:0.01 | 1:100 to 1:0.2 |
| (19-26) | pyribencarb | 1:100 to 1:0.01 | 1:100 to 1:0.2 |
| (19-27) | 3-[5-(4-chlorophenyl)-2,3-dimethyl-3-isoxazolidinyl]pyridine | 1:100 to 1:0.01 | 1:100 to 1:0.2 |
| Group (20): | (thio)urea derivatives | 1:100 to 1:0.01 | 1:5 to 1:0.01 |
| Group (21): | amides | 1:100 to 1:0.01 | 1:5 to 1:0.01 |
| Group (22): | triazolopyrimidines | 1:100 to 1:0.01 | 1:5 to 1:0.01 |
| Group (23): | iodochromones | 1:100 to 1:0.01 | 1:5 to 1:0.01 |

In each case, the mixing ratio is to be chosen such that a synergistic mixture is obtained. The mixing ratios between the compound of group (1) and a compound from one of groups (2) to (23) may also vary between the individual compounds of a group.

The active compound combinations according to the invention have very good fungicidal properties and can be used for controlling phytopathogenic fungi, such as Plasmodiophoromycetes, Oomycetes, Chytridiomycetes, Zygomycetes, Ascomycetes, Basidiomycetes, Deuteromycetes, etc.

Some pathogens causing fungal and bacterial diseases which come under the generic names listed above may be mentioned as examples, but not by way of limitation:

diseases caused by powdery mildew pathogens, such as, for example,

*Blumeria* species, such as, for example, *Blumeria graminis*;

*Podosphaera* species, such as, for example, *Podosphaera leucotricha*;

*Sphaerotheca* species, such as, for example, *Sphaerotheca fuliginea*;

*Uncinula* species, such as, for example, *Uncinula necator*;

diseases caused by rust disease pathogens, such as, for example,

*Gymnosporangium* species, such as, for example, *Gymnosporangium sabinae*

*Hemileia* species, such as, for example, *Hemileia vastatrix*;

*Phakopsora* species, such as, for example, *Phakopsora pachyrhizi* and *Phakopsora meibomiae*;

*Puccinia* species, such as, for example, *Puccinia recondita*;

*Uromyces* species, such as, for example, *Uromyces appendiculatus*;

diseases caused by pathogens from the group of the Oomycetes, such as, for example,

*Bremia* species, such as, for example, *Bremia lactucae*;

*Peronospora* species, such as, for example, *Peronospora pisi* or *P. brassicae*;

*Phytophthora* species, such as, for example *Phytophthora infestans*;

*Plasmopara* species, such as, for example, *Plasmopara viticola*;

*Pseudoperonospora* species, such as, for example, *Pseudoperonospora humuli* or *Pseudoperonospora cubensis*;

*Pythium* species, such as, for example, *Pythium ultimum*;

leaf blotch diseases and leaf wilt diseases caused, for example, by

*Alternaria* species, such as, for example, *Alternaria solani*;

*Cercospora* species, such as, for example, *Cercospora beticola*;

*Cladiosporum* species, such as, for example, *Cladiosporium cucumerinum*;

*Cochliobolus* species, such as, for example, *Cochliobolus sativus* (conidia form: *Drechslera*, Syn: *Helminthosporium*);

*Colletotrichum* species, such as, for example, *Colletotrichum lindemuthianum*;

*Cycloconium* species, such as, for example, *Cycloconium oleaginum*;

*Diaporthe* species, such as, for example, *Diaporthe citri*;

*Elsinoe* species, such as, for example, *Elsinoe fawcettii*;

*Gloeosporium* species, such as, for example, *Gloeosporium laeticolor*;

*Glomerella* species, such as, for example, *Glomerella cingulata*;

*Guignardia* species, such as, for example, *Guignardia bidwelli*;

*Leptosphaeria* species, such as, for example, *Leptosphaeria maculans*;

*Magnaporthe* species, such as, for example, *Magnaporthe grisea*;

*Mycosphaerella* species, such as, for example, *Mycosphaerella graminicola*;

*Phaeosphaeria* species, such as, for example, *Phaeosphaeria nodorum*;

*Pyrenophora* species, such as, for example, *Pyrenophora teres*;

*Ramularia* species, such as, for example, *Ramularia collo-cygni*;

*Rhynchosporium* species, such as, for example, *Rhynchosporium secalis*;

*Septoria* species, such as, for example, *Septoria apii*;

*Typhula* species, such as, for example, *Typhula incarnata*;

*Venturia* species, such as, for example, *Venturia inaequalis*;

root and stem diseases caused, for example, by

*Corticium* species, such as, for example, *Corticium graminearum*;

*Fusarium* species, such as, for example, *Fusarium oxysporum*;

*Gaeumannomyces* species, such as, for example, *Gaeumannomyces graminis*;

*Rhizoctonia* species, such as, for example *Rhizoctonia solani*;

*Tapesia* species, such as, for example, *Tapesia acuformis*;

*Thielaviopsis* species, such as, for example, *Thielaviopsis basicola*;

ear and panicle diseases (including maize crops) caused, for example, by

*Alternaria* species, such as, for example, *Alternaria* spp.;

*Aspergillus* species, such as, for example, *Aspergillus flavus*;

*Cladosporium* species, such as, for example, *Cladosporium* spp.;

*Claviceps* species, such as, for example, *Claviceps purpurea*;

*Fusarium* species, such as, for example, *Fusarium culmorum*;

*Gibberella* species, such as, for example, *Gibberella zeae*;

*Monographella* species, such as, for example, *Monographella nivalis*;

diseases caused by smut fungi, such as, for example,

*Sphacelotheca* species, such as, for example, *Sphacelotheca reiliana*;

*Tilletia* species, such as, for example, *Tilletia caries*;

*Urocystis* species, such as, for example, *Urocystis occulta*;

*Ustilago* species, such as, for example, *Ustilago nuda*;

fruit rot caused, for example, by

*Aspergillus* species, such as, for example, *Aspergillus flavus*;

*Botrytis* species, such as, for example, *Botrytis cinerea*;

*Penicillium* species, such as, for example, *Penicillium expansum*;

*Sclerotinia* species, such as, for example, *Sclerotinia sclerotiorum*;

*Verticilium* species, such as, for example, *Verticilium alboatrum*;

seed- and soil-borne rot and wilt diseases, and also diseases of seedlings, caused, for example, by

*Fusarium* species, such as, for example, *Fusarium culmorum*;

*Phytophthora* species, such as, for example, *Phytophthora cactorum*;

*Pythium* species, such as, for example, *Pythium ultimum*;

*Rhizoctonia* species, such as, for example, *Rhizoctonia solani*;

*Sclerotium* species, such as, for example, *Sclerotium rolfsii*;

cancerous diseases, galls and witches' broom caused, for example, by

*Nectria* species, such as, for example, *Nectria galligena*;

wilt diseases caused, for example, by

*Monilinia* species, such as, for example, *Monilinia laxa*;

deformations of leaves, flowers and fruits caused, for example, by

*Taphrina* species, such as, for example, *Taphrina deformans*;

degenerative diseases of woody plants caused, for example, by

*Esca* species, such as, for example, *Phaemoniella clamydospora*;

diseases of flowers and seeds caused, for example, by

*Botrytis* species, such as, for example, *Botrytis cinerea*;

diseases of plant tubers caused, for example, by

*Rhizoctonia* species, such as, for example, *Rhizoctonia solani*;

diseases cause by bacterial pathogens, such as, for example,

*Xanthomonas* species, such as, for example *Xanthomonas campestris* pv. *oryzae*;

*Pseudomonas* species, such as, for example, *Pseudomonas syringae* pv. *lachrymans*;

*Erwinia* species, such as, for example, *Erwinia amylovora*.

With preference, it is possible to control the following diseases of soya beans:

fungal diseases on leaves, stems, pods and seeds, caused, for example, by alternaria leaf spot (*Alternaria* spec. atrans *tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*);

fungal diseases on roots and the stem base, caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compound combinations according to the invention are particularly suitable for controlling diseases caused by rust disease pathogens, such as, for example, *Phakopsora* species, such as, for example, *Phakopsora pachyrhizi* and *Phakopsora meibomiae*.

Preference is given to controlling the following diseases of soya beans:

fungal diseases on leaves, stems, pods and seeds caused by rust (*Phakopsora pachyrhizi* and *Phakopsora meibomiae*). Especially preferred is the control of *Phakopsora pachyrhizi*.

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application or else as seed dressings.

A large part of the damage to crop plants which is caused by phytopathogenic fungi occurs as early as when the seed is attacked during storage and after the seed is introduced into the soil, as well as during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fungi by treating the seeds of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants or where additional application is at least reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the composition according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that, by virtue of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of seed of cereals (such as wheat, barley, rye and oats), maize and rice is of particular importance. Furthermore, the treatment of seed of soya beans is of particular importance.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations according to the invention are also suitable for increasing the yield of crops. In addition, they show reduced toxicity and are well tolerated by plants.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment according to the invention of the plants and parts of the plants (including seed) with the active compound combination is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one or multiple-layer coating. Here, the active compound combinations can be prepared prior to the treatment by mixing the individual active compounds, and they are thus applied as a mixture. Alternatively, the treatment is carried out successively by initially using one herbicide of group (1) followed by treatment with an active compound of groups (2) to (23). However, it is also possible to initially treat the plants or plant parts (including seed) with an active compound of groups (2) to (23), followed by treatment with a herbicide of group (1). In particular, it is also possible to initially provide seed with a one- or multi-layer coating of one or more active compounds of groups (2) to (23) and to spray the resulting plants only after emergence of an infection with a herbicide of group (1) (for example seed of soya bean or maize is initially treated with fluquinconazole or carboxin, followed by later foliar application of glyphosate; or seed of oilseed rape is initially treated with fluquinconazole or carboxin, followed by later foliar application of glufosinate).

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defense of the plants against insects, by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), Starlink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

Depending on their particular physical and/or chemical properties, the active compound combinations according to the invention can be converted into the customary formulations, such as solutions, emulsions, suspensions, powders, dusts, foams, pastes, soluble powders, granules, aerosols, suspoemulsion concentrates, natural and synthetic materials impregnated with active compound and microencapsulations in polymeric substances and in coating compositions for seeds, and ULV cool and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The active compound content of the use forms prepared from the commercial formulations may be varied within wide ranges. The concentration of active compound of the use forms for controlling animal pests, such as insects and acarids, may be from 0.0000001 to 95% by weight of active compound and is preferably from 0.0001 to 1% by weight. Application is in a customary manner adapted to the use forms.

The formulations for controlling unwanted phytopathogenic fungi generally comprise between 0.1 and 95% by weight of active compounds, preferably between 0.5 and 90%.

The active compound combinations according to the invention can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, painting, spreading-on, and as a powder for dry seed treatment, a solution for seed treatment, a water-soluble powder for seed treatment, a water-soluble powder for slurry treatment, or by encrusting etc.

The active compound combinations according to the invention can, in commercial formulations and in the use forms prepared from these formulations, be present as a mixture with other active compounds, such as insecticides, attractants, sterilants, bactericides, acaricides, nematicides, fungicides, growth regulators or herbicides.

When using the active compound combinations according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seed, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The active compound combinations can be used as such, in the form of concentrates or in the form of generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and, if desired, colorants and pigments and other processing auxiliaries.

The good fungicidal action of the active compound combinations according to the invention is demonstrated by the examples below. While the individual active compounds show weaknesses in their fungicidal action, the combinations show an action which exceeds a simple sum of actions.

A synergistic effect in fungicides is always present when the fungicidal activity of the active compound combinations exceeds the total of the activity of the active compounds when applied individually.

The expected fungicidal action for a given combination of two active compounds can be calculated as follows, according to S. R. Colby ("Calculating Synergistic and Antagonistic Responses of Herbicide Combinations", Weeds 1967, 15, 20-22):

If

X is the efficacy when employing active compound A at an application rate of m g/ha, Y is the efficacy when employing active compound B at an application rate of n g/ha, E is the efficacy when employing active compounds A and B at application rates of m and n g/ha then $$E = X + Y - \frac{X \times Y}{100}$$

Here, the efficacy is determined in %. 0% means an efficacy which corresponds to that of the control, whereas an efficacy of 100% means that no infection is observed.

If the actual fungicidal activity exceeds the calculated value, the activity of the combination is superadditive, i.e. a synergistic effect is present. In this case, the actually observed efficacy must exceed the value calculated using the above formula for the expected efficacies (E).

The invention is illustrated by the examples below. However, the invention is not limited to the examples.

EXAMPLES

Example A

*Phytophthora* Test (Tomato)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Phytophthora infestans*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

Example B

*Plasmopara* Test (Grapevine)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabinet at about 20° C. and 100% relative atmospheric humidity for 1 day. The plants are then placed in a greenhouse at about 21° C. and about 90% atmospheric humidity for 4 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

Example C

*Podosphaera* Test (Apple)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Example D

*Sphaerotheca* Test (Cucumber)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Example E

*Uncinula* Test (Grapevines)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Uncinula* necator. The plants are then placed in a greenhouse at about 23° C. and a relative atmospheric humidity of about 70%.

Evaluation is carried out 14 days after the inoculation. 0% means an efficacy which corresponds to that of the control, whereas an efficacy of 100% means that no infection is observed.

Example F

*Uromyces* Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the rust pathogen *Uromyces appendiculatus* and then remain in an incubation cabin at about 20° C. and 100% relative atmospheric humidity for 1 day. The plants are then placed in a greenhouse at about 23° C. and a relative atmospheric humidity of about 90%.

Evaluation is carried out 10 days after the inoculation. 0% means an efficacy which corresponds to that of the control, whereas an efficacy of 100% means that no infection is observed.

Example G

*Phakopsora* Test (Soya Bean)

The suitable active compound preparations used are commercial formulations which, if required, are diluted to the desired concentration prior to application.

Soya bean plants (cv. Miyagishirome) are cultivated in a plastic vessel having a diameter of 7.5 cm for 14 days, until they have reached the ⅔-leaf stage. The active compound preparations were, at the concentrations stated below, sprayed onto the test plants (6 ml for in each case 3 test vessels, the test solution contains 0.02% of Neoesterin as tackifier).

1 day after the application of the active compound preparation, the plants were sprayed with a urediniospore suspension ($1 \times 10^5$ urediniospores/ml) of the rust pathogen *Phakopsora pachyrhizi*. The plants are then placed in a greenhouse at about 25° C. during the day and about 18° C. at night and a relative atmospheric humidity of 91.9%.

Evaluation is carried out 11 days after the inoculation by comparison of the infected areas of untreated and treated plants. 0% means an efficacy which corresponds to that of the control, whereas an efficacy of 100% means that no infection is observed.

TABLE G

Phakopsora test (soya beans)

| Active compounds | Application rate of active compound in ppm | Efficacy in % found* | calc.** |
|---|---|---|---|
| (1-1) glyphosate | 0.5 | 0 | |
| | 5 | 0 | |

TABLE G-continued

Phakopsora test (soya beans)

| Active compounds | Application rate of active compound in ppm | Efficacy in % found* | calc.** |
|---|---|---|---|
| (3-17) tebuconazole | 0.5 | 50 | |
| (1-1) + (3-17) (1:1) | 0.5 + 0.5 | 96 | 50 |
| (1-1) + (3-17) (10:1) | 5 + 0.5 | 99 | 50 |
| (1-2) glufosinate | 0.5 | 0 | |
| | 5 | 0 | |
| (3-17) tebuconazole | 0.5 | 60 | |
| (1-2) + (3-17) (1:1) | 0.5 + 0.5 | 94 | 60 |
| (1-2) + (3-17) (10:1) | 5 + 0.5 | 95 | 60 |

*found = activity found
**calc. = activity calculated using Colby's formula

Example H

*Venturia* Test (Apple)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day. The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Example I

*Alternaria* Test (Tomato)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Alternaria solani*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

Example J

Botrytis Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

The size of the infected areas on the leaves is evaluated 2 days after the inoculation. 0% means an efficacy which corresponds to that of the control, whereas an efficacy of 100% means that no infection is observed.

Example K

Erysiphe Test (Barley)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of *Erysiphe graminis* f. sp. *hordei*. The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Example L

Erysiphe Test (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of *Erysiphe graminis* f. sp. *tritici*. The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Example M

Fusarium Culmorum Test (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Fusarium culmorum*. The plants are placed in a greenhouse under transparent incubation hoods at a temperature of about 20° C. and a relative atmospheric humidity of about 100%.

Evaluation is carried out 4 days after the inoculation. 0% means an efficacy which corresponds to that of the control, whereas an efficacy of 100% means that no infection is observed.

Example N

Fusarium Nivale (Var. Majus) Test (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Fusarium nivale* (var. *majus*).

The plants are placed in a greenhouse under transparent incubation hoods at a temperature of about 15° C. and a relative atmospheric humidity of about 100%.

Evaluation is carried out 4 days after the inoculation. 0% means an efficacy which corresponds to that of the control, whereas an efficacy of 100% means that no infection is observed.

Example O

Fusarium Graminearum Test (Barley)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Fusarium graminearum*.

The plants are placed in a greenhouse under transparent incubation hoods at a temperature of about 15° C. and a relative atmospheric humidity of 100%.

69

Evaluation is carried out 4 days after the inoculation. 0% means an efficacy which corresponds to that of the control, whereas an efficacy of 100% means that no infection is observed.

Example P

*Leptosphaeria Nodorum* Test (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of 80%.

Evaluation is carried out 10 days after the inoculation. 0% means an efficacy which corresponds to that of the control, whereas an efficacy of 100% means that no infection is observed.

Example Q

*Pseudocercosporella Herpotrichoides* Test; R Strain (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, the young plants are sprayed with the preparation of active compound at the stated application rate. After the spray coating has dried on, the plants are inoculated at the base of the stem with spores of the R strain of *Pseudocercosporella herpotrichoides*.

The plants are placed in a greenhouse at a temperature of about 10° C. and a relative atmospheric humidity of 80%.

Evaluation is carried out 21 days after the inoculation. 0% means an efficacy which corresponds to that of the control, whereas an efficacy of 100% means that no infection is observed.

Example R

*Pseudocercosporella Herpotrichoides* Test; W Strain (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, the young plants are sprayed with the preparation of active compound at the stated application rate. After the spray coating has dried on, the plants are inoculated at the base of the stem with spores of the W strain of *Pseudocercosporella herpotrichoides*.

The plants are placed in a greenhouse at a temperature of about 10° C. and a relative atmospheric humidity of 80%.

Evaluation is carried out 21 days after the inoculation. 0% means an efficacy which corresponds to that of the control, whereas an efficacy of 100% means that no infection is observed.

Example S

*Puccinia* Test (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

Example T

*Pyrenophora Teres* Test (Barley)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 7 days after the inoculation. 0% means an efficacy which corresponds to that of the control, whereas an efficacy of 100% means that no infection is observed.

The invention claimed is:

1. An active compound combination, comprising synergistically effective amounts of a herbicide selected from the group consisting of
    (1-2) glufosinate and
    (1-3) glufosinate-ammonium
    and at least one strobilurin selected from groups consisting of
    (2-1) azoxystrobin, (2-2) fluoxastrobin, (2-3) (2E)-2-(2-{[6-(3-chloro-2-methylphenoxy)-5-fluoro-4-pyrimidinyl]oxy}phenyl)-2-(methoxyimino)-N-methylethanamide, (2-4) trifloxystrobin, (2-5) (2E)-2-(methoxyimino)-N-methyl-2-(2-{[({(1E)-1-[3-

(trifluoromethyl)phenyl]ethylidene}amino)oxy]methyl}phenyl)ethanamide, (2-6) (2E)-2-(methoxyimino)-N-methyl-2-{2-[(E)-({1-[3-(trifluoromethyl)phenyl]ethoxy}imino)-methyl]phenyl}ethanamide, (2-7) orysastrobin, (2-8) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2-9) kresoxim-methyl, (2-10) dimoxystrobin, (2-11) picoxystrobin, (2-12) pyraclostrobin, (2-13) metominostrobin, (2-14) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, and (2-15) enestroburin,
wherein the ratio of the herbicide to the at least one strobilurin is from 1:100 to 1:0.01.

2. The active compound combination according to claim 1, wherein said herbicide is (1-2) glufosinate.

3. The active compound combination according to claim 1, wherein said herbicide is (1-3) glufosinate-ammonium.

4. A method of treating a transgenic plant comprising applying an active compound combination according to claim 1 to the transgenic plant.

5. The method according to claim 4, wherein the transgenic plant is resistant to glufosinate or glufosinate-ammonium.

6. A method for controlling unwanted phytopathogenic fungi, comprising applying an active compound combination according to claim 1 to the unwanted phytopathogenic fungi, their habitat or to the seed of a plant.

7. A method of controlling a rust disease on a soya bean plant comprising applying an active compound combination according to claim 1 to a soya bean plant.

8. The method according to claim 4 wherein the transgenic plant is a transgenic soya bean plant.

9. The method according to claim 8, wherein said transgenic soya bean plant is resistant to glufosinate or glufosinate-ammonium.

10. The method according to claim 6 wherein the unwanted phytopathogenic fungi is rust fungi.

11. A method of treating a seed comprising applying an active compound combination according to claim 1 to a seed.

12. The method according to claim 11 wherein the seed is a seed of a transgenic plant.

13. The method of claim 4 wherein the transgenic plant is an herbicide-resistant plant.

14. The method of claim 4 wherein the transgenic plant is an herbicide-sensitive plant.

15. The active compound combination according to claim 1 wherein the ratio of the herbicide to the at least one strobilurin is from 1:5 to 1:0.01.

16. The active compound combination according to claim 1 wherein the at least one strobilurin is pyraclostrobin.

17. The active compound combination according to claim 1 wherein the at least one strobilurin is trifloxystrobin.

18. The active compound combination according to claim 1 wherein the at least one strobilurin is fluoxastrobin.

19. The method according to claim 12 wherein the seed is seed of a transgenic soya bean plant.

20. A process for preparing a fungicidal composition comprising mixing the active compound combination according to claim 1 with extenders and/or surfactants.

21. The active compound combination according to claim 1 further comprising seed.

22. The method according to claim 4 wherein the transgenic plant is a transgenic cereal plant.

23. The method according to claim 22, wherein said transgenic cereal plant is wheat or barley.

24. The method according to claim 22, wherein said transgenic cereal plant is resistant to glufosinate or glufosinate-ammonium.

25. The method according to claim 12, wherein the seed is seed of a transgenic cereal plant.

26. The method according to claim 25, wherein said transgenic cereal plant is wheat or barley.

27. The active compound combination of claim 1, wherein the ratio of the herbicide to the at least one strobilurin is from 1:100 to 1:5.

* * * * *

UNITED STATES PATENT AND TRADEMARK OFFICE
CERTIFICATE OF CORRECTION

| | | |
|---|---|---|
| PATENT NO. | : 8,754,009 B2 | Page 1 of 1 |
| APPLICATION NO. | : 11/921667 | |
| DATED | : June 17, 2014 | |
| INVENTOR(S) | : Stenzel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1076 days.

Signed and Sealed this
Twenty-sixth Day of January, 2016

Michelle K. Lee
*Director of the United States Patent and Trademark Office*